(12) United States Patent
McHale et al.

(10) Patent No.: US 6,812,204 B1
(45) Date of Patent: Nov. 2, 2004

(54) DELIVERY OF AN AGENT

(75) Inventors: Anthony Patrick McHale, County Londonderry (GB); Roger Craig, Smallwood (GB); Ana Maria Rollan Haro, Londonderry (GB)

(73) Assignee: Gendel Limited, Oxon (GB)

( * ) Notice: Subject to any disclaimer, the term of this patent is extended or adjusted under 35 U.S.C. 154(b) by 64 days.

(21) Appl. No.: 09/748,063

(22) Filed: Dec. 22, 2000

Related U.S. Application Data

(63) Continuation-in-part of application No. PCT/GB00/02848, filed on Jul. 24, 2000.
(60) Provisional application No. 60/146,556, filed on Jul. 30, 1999.

(51) Int. Cl.[7] .................... A61K 31/00; C12N 12/87
(52) U.S. Cl. .................... 514/2; 435/461; 435/470; 435/173.1; 435/173.4; 435/173.5; 435/173.6; 435/173.7
(58) Field of Search ............... 514/2; 435/461, 435/470, 173.1, 173.4, 173.5–173.7

(56) References Cited

U.S. PATENT DOCUMENTS

| | | | |
|---|---|---|---|
| 4,224,313 A | 9/1980 | Zimmermann et al. | |
| 4,935,223 A | 6/1990 | Phillips | |
| 5,236,835 A | 8/1993 | Mouneimne et al. | |

FOREIGN PATENT DOCUMENTS

| | | | | |
|---|---|---|---|---|
| EP | 0 367 475 A2 | 5/1990 | | |
| EP | 0 882 448 A1 | 12/1998 | | |
| EP | 0 898 889 A1 | 3/1999 | | |
| WO | WO 97/33474 | 9/1997 | | |
| WO | WO 97/49450 | * 12/1997 | ............ | A61N/1/30 |
| WO | WO 98/52609 | 11/1998 | | |

OTHER PUBLICATIONS

Fields et al (In Fundamental Virology, Second Edition, Raven Press, New York, 1991).*
T. Ward et al., "The effects of electric fields on photosensitized erythrocytes: possible enhancement of photodynamic activation", Cancer Letters, vol. 106, pp. 69–74, Aug. 23, 1996, referred to as XP–000857165*.
Chemical Abstracts, vol. 90, No. 1, Jan. 1, 1979, Columbus, Ohio, US, Abstract No. 3815p, A.R. Williams et al., "Release of β–thromboglobulin from human platelets by therapeutic intensities of ultrasound", p. 373, col. 2, abstract & BR. J. Haematol., vol. 40, No. 1, 1978, pp. 133–142.
Y. Mouneimne et al., "Electro–Insertion of Xeno–Glycophorin Into the Red Blood Cell Membrane", Biochemical and Biophysical Research Communications, vol. 159, No. 1, pp. 34–40, Feb. 28, 1989, referred to as XP–002166099*.
Brayman, et al., "Re–evaluation of the Concept that High Cell Concentrations "Protect" Cells In Vitro From Ultrasonically Induced Lysis," *Ultrasound in Med. and Biol*, vol. 23, No. 4, p497–514 (1996).
Flynn, et al., "Methotrexate–loaded, Photosensitized Erythrocytes: A Photo–Activatable Carrier/Delivery System for Use in Cancer Therapy," *Cancer Letters*, 82, p225–229 (1994).

* cited by examiner

*Primary Examiner*—Dave T. Nguyen
*Assistant Examiner*—Richard Schnizer
(74) *Attorney, Agent, or Firm*—Frommer Lawrence & Haug; Thomas J. Kowalski; Deborah Lu

(57) ABSTRACT

The invention relates to a method for selectively releasing an agent loaded into a red blood cell, comprising electrosensitizing the red blood cell by application of an electric field and subsequently disrupting the cell selectively using ultrasound.

18 Claims, 20 Drawing Sheets

+U/S        -U/S

RbRBC + Electrosensitisation

RbRBC unmodified

RbRBC plus 2.5% glutaraldehyde

RbRBC PEGylated

*in vivo* survival of modified erythrocytes in rabbit

Survival of loaded and sensitised rabbit erythroyctes in circulation

DELIVERY OF AN AGENT

This application is a continuation-in-part ("CIP") of International application No. PCT/GB00/02848, filed Jul. 24, 2000, which claims priority from U.S. provisional application Ser. No. 60/146,556, filed Jul. 30, 1999 and G.B. application Serial No. 9917416.1, filed Jul. 23, 1999.

FIELD OF THE INVENTION

The present invention relates to a method for delivering an agent to a target site.

BACKGROUND OF THE INVENTION

The delivery of a therapeutic agents to specific tissues is desirable typically to ensure that a sufficiently high dose of a given agent is delivered to a selected tissue. Moreover, it is often the case that the therapeutic agent, although advantageously having beneficial therapeutic effects on the diseased tissue, may have undesirable side effects on tissues that are not diseased. For example, in the treatment of certain types of disorders, such as cancer, it is necessary to use a high enough dose of a drug to kill the cancer cells without killing an unacceptable high number of normal cells. Thus, one of the major challenges of disease treatment is to identify ways of exploiting cellular drug delivery vehicles to incorporate and to selectively release agents at a desired target site.

It has been suggested that red blood cells may be exploited as active agent/drug delivery vehicles (DeLoach & Sprandel 1985, Bibliotheca Haematologica; Publ. Karger, Munich) as it is possible to incorporate agents into human red blood cells using a variety of techniques. An example of such a technique is the exploitation of osmotic shock and modifications thereof such as hypotonic shock and subsequent recovery of isotonicity and reverse hypotonic dialysis (Luque & Pinilla, 1993, Ind. Farmac. 8, 53–59).

An alternative method for loading drugs and active agents into red blood cells is electroporation. Using this process, the agent of interest are mixed with the live red blood cells in a buffer medium and short pulses of high electric fields are applied. The red blood cell membranes are transiently made porous and the agents of interest enter the cells. The electroporation process is advantageous as very high loading indices can be achieved within a very short time period (Flynn et al., 1994, Cancer Letts., 82, 225–229).

When packaging/carrier/delivery systems such as red blood cells are used as in vivo delivery systems, they suffer from the drawback that the delivery function is dependent upon both an accumulation of the red blood cells and a breakdown of the red blood cell membrane in or at the relevant tissue/site. As a result, attempts have been made to incorporate sensitizing agents into cell carriers in order to facilitate both the accumulation and/or release of an agent of interest at a target site.

Alternative energy sources have been investigated as tools for inducing payload release from loaded and sensitized cells. By way of example, ultrasound irradiation has been investigated as an alternative to light induced photodynamic activation as it has a broader degree of focus and it penetrates more deeply into the body. However, although ultrasound irradiation has also been applied to effect red blood cell lysis in vitro, its use has been limited in that its effect is only significant at lower cell concentrations ($1-6 \times 10^6$ cells) (Brayman et at., 1996, Ultrasound in Med & Biol., 22: 497–514). Moreover, ultrasound is non-specific in effects, resulting in lysis of both loaded and endogenous red blood cells.

Recently, it has been found that certain dye compounds, in particular porphyrins, can achieve a cytopathogenic effect when the disease site is subjected to ultrasound irradiation. This technique is referred to as sonodynamic therapy and is discussed in WO98/52609. WO98/52609 teaches that ultrasound irradiation may be useful in treating disease but only when it is combined with an effective amount of an ultrasound-susceptibility modification agent such as a porphyrin.

SUMMARY OF THE INVENTION

The present invention provides a method for selectively releasing an agent from a loaded red blood cell at a target site.

According to a first aspect of the present invention, we provide the use of an electric field for sensitizing a red blood cell to ultrasound.

Preferably, the electric field is used in a method which comprises the steps of: providing a red blood cell and subjecting the red blood cell to an electric field, the electric field having sufficient energy to electrosensitize the cell. More preferably, the red blood cell sensitized using electric field pulsing may be selectively disrupted using ultrasound.

According to a second aspect of the invention, we provide a method of selectively disrupting a red blood cell, the method comprising the steps of: (a) providing a red blood cell; (b) electrosensitizing said red blood cell; and (c) disrupting said red blood cell by subjecting said red blood cell to ultrasound.

Preferably, the use according to the first aspect of the invention and the method according to the second aspect of the invention is such that the electrosensitization comprises the step of applying an electric pulse to a red blood cell. Preferably, the electric pulse is from about 0.1 kVolts/cm to about 10 kVolts/cm under in vitro conditions.

The method or use according to the first and second aspects of the invention may further comprise the step of loading the red blood cell with an agent.

The sensitization of the red blood cell may precede the loading of the agent. Alternatively, the loading of the agent precedes the sensitization of the red blood cell. In yet another alternative, the sensitization of the red blood cell and the loading of the agent are substantially simultaneous.

According to a third aspect of the invention, we provide a method for selectively releasing an agent from a red blood cell comprising the steps of: loading a red blood cell with an agent; electrosensitizing the red blood cell; and causing the agent to be released from the electrosensitized red blood cell by applying ultrasound at a frequency and energy sufficient to cause disruption of the red blood cell but insufficient to cause disruption of unsensitized red blood cells.

According to a fourth aspect of the present invention, there is provided a method for delivering an agent to a target site in a vertebrate, comprising the steps of: providing a red blood cell; loading the red blood cell with an agent; electrosensitizing the red blood cell; introducing the sensitized red blood cell into the vertebrate; and causing the disruption of the sensitized red blood cell by treatment of the cell with ultrasound to release the agent at a target site.

According to a fifth aspect of the present invention, there is provided a method for electrosensitizing a red blood cell, comprising the steps of: providing a red blood cell; and subjecting the red blood cell to an electric field, the electric field having sufficient energy to electrosensitize the cell.

The electrosensitized red blood cells according to the invention may be loaded with agents either before, during or after the electrosensitization procedure. In one aspect, therefore, the electrosensitization procedure is effective to electroporate the cells, thus effecting simultaneous loading of a desired agent. Preferably, however, the electrosensitization procedure is not effective to electroporate the cells, and the loading is thus carried out in a separate step either before or after the electrosensitization procedure. Preferred methods for loading cells are set out below.

According to a sixth aspect of the invention, there is provided an electrosensitized red blood cell which is preparable by subjecting a red blood cell to an electric field at an energy level which is not effective to electroporate the cell. The invention also provides electrosensitized red blood cells according to the fourth aspect, which have been loaded with an agent using a process other than electroporation.

According to a seventh aspect of the present invention, there is provided a kit comprising a red blood cell, an agent, packaging materials therefor and instructions for use, the use comprising the steps of: electrosensitizing a red blood; loading the red blood cell with an agent; causing the agent to be released from the electrosensitized red blood cell by exposure to ultrasound at a frequency and energy effective to cause disruption of the sensitized red blood cell but insufficient to cause disruption of unsensitized red blood cells.

According to a eighth aspect of the present invention, there is provided a kit comprising a red blood cell which is loaded with an agent, packaging materials therefor and instructions for use comprising the steps of: electrosensitizing a red blood cell; and causing the agent to be released from the sensitized red blood cell by exposure to ultrasound at a frequency and energy effective to cause disruption of the sensitized red blood cell but insufficient to cause disruption of unsensitized red blood cells.

According to a ninth aspect of the present invention, there is provided a kit comprising a loaded electrosensitized red blood and instructions for causing the agent to be released from the electrosensitized red blood cell by exposure to ultrasound at a frequency and energy effective to cause disruption of the sensitized red blood cell but insufficient to cause disruption of unsensitized red blood cells.

In these and other aspects of the invention, the sensitization and loading steps may be performed in any desired order, as appropriate.

DETAILED DESCRIPTION OF THE INVENTION

Figure 1:
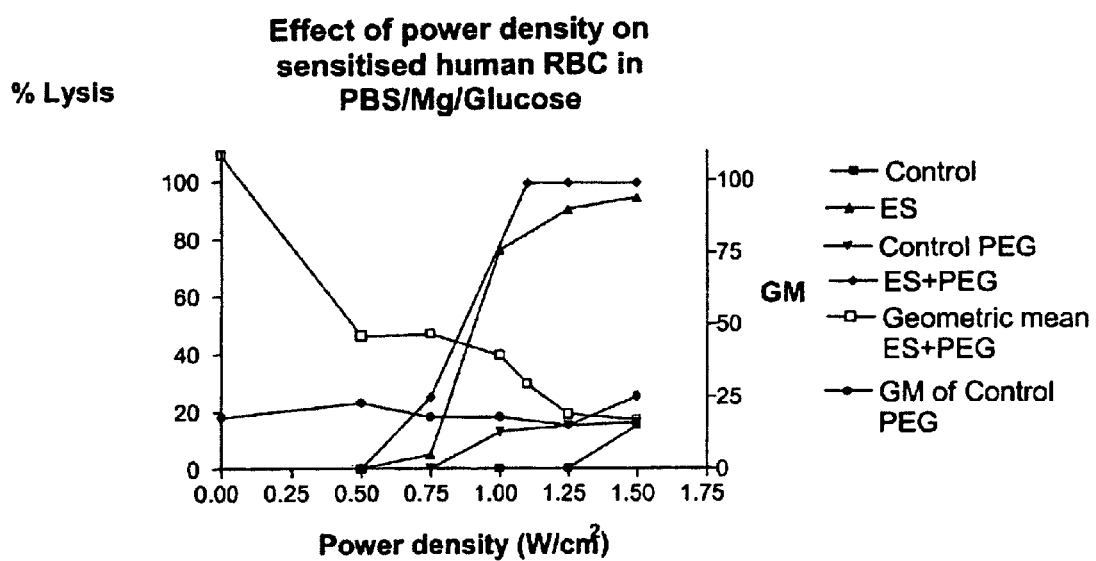
FIG. 1 shows the effect of ultrasound power density on control normal (■), electrosensitized normal (▲), control PEG-treated (▼), and electrosensitized PEG-treated human red blood cells in PBS/Mg/glucose. X-axis: power density (W/cm$^2$); left hand Y-axis: % lysis. The geometric mean (right-hand Y-axis) of fluorescence from populations of PEG-treated control (●) and electrosensitized PEG-treated human red blood cells exposed to each power density and determined using flow cytometry are also plotted.

The present invention demonstrates the novel and unobvious findings that:

(i) exposure of red blood cells to electrosensitization induces a hyper-sensitivity to ultrasound.

(ii) exposure of red blood cells to electrosensitization induces a hyper-sensitivity to ultrasound without the addition of chemical agents.

(iii) exposure of red blood cells to electrosensitization induces a hyper-sensitivity to ultrasound and allows the selective lysis of destabilized red blood cells with ultrasound with little or no effect on normal red blood cells under in vitro and in vivo conditions.

(iv) the present invention allows for the targeted delivery of an agent to a tissue of interest in a vertebrate using sensitized red blood cells which have no particular affinity for the target tissue. This is of particular importance where the target tissue is of a type which is widely distributed throughout the body (for example, skeletal muscle).

Electrosensitization

The terms "sensitized", "sensitization" and "electrosensitization" encompass the destabilization of cells without causing fatal damage to the cells. A momentary exposure of a cell to a high electric field results in membrane destabilization. The strength of the electric field is adjusted up or down depending upon the resilience or fragility, respectively, of the cells being loaded and the ionic strength of the medium in which the cells are suspended. The sensitized cells display a hyper-sensitivity relative to un-sensitized cells, to for example, ultrasound or light energy.

Electrosensitization typically involves the use of electric fields which do not possess sufficient energy to electroporate the cells. Electroporation, which facilitates the passage of agents into the cell without significant loss of cellular contents or cell viability, is well known in the art, and apart from the energy levels involved is similar to electrosensitization. Indeed, cells which are electroporated become electrosensitized. However, electrosensitization may be carried out at energy levels which are insufficient to electroporate the cell and permit the passage of substances through the cell wall. Thus, the invention encompasses the use of an electric field for sensitizing a red blood cell to ultrasound.

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

These known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 μs duration. Such a pulse may be generated, for example, in known applications of the Electro Square Porator T820.

Electrosensitization may be performed in a manner substantially identical to the procedure followed for electroporation, with the exception that lower electric field strengths may be used, as set forth below.

In a preferred aspect of the present invention, the electric field has a strength of from about 0.1 kVolts/cm to about 10 kVolts/cm under in vitro conditions.

Preferably the electric field has a strength of from about 1.5 kVolts/cm to about 4.0 kVolts/cm under in vitro conditions.

Preferably the electric field has a strength of from about 0.1 kVolts/cm to about 10 kVolts/cm under in vivo conditions (see WO97/49450).

Preferably the application of the electric field comprises multiple pulses.

Preferably the application of the electric field comprises sequential pulses (see Table 1).

Preferably the application of the electric field comprises double pulses.

Preferably the electric pulse is delivered as an exponential wave form.

Preferably the electric pulse is delivered as a square wave form.

Preferably the electric pulse is delivered as a modulated wave form.

As used herein, the term "electric pulse" includes one or more pulses at variable capacitance and voltage and including exponential and/or square wave and/or modulated wave forms.

Other electroporation procedures and methods employing electroporation devices are widely used in cell culture, and appropriate instrumentation is well known in the art.

Loading

As used herein, the term "loading" refers to a red blood cell which comprises at least one agent. The agent may be loaded by becoming internalized by, affixed to the surface of, or anchored into the plasma membrane of a red blood cell. Where the agent is affixed or anchored to the plasma membrane, loading may be achieved by cross-linking the agent to any cell surface molecule. Alternatively, the agent may be conjugated to or fused with an antibody specific for a cell surface molecule.

Loading of a red blood cell with more than one agent may be performed such that the agents are loaded individually (in sequence) or together (simultaneously or concurrently) and/or prior to, simultaneous with, sequential to or separate from, the "sensitizing" procedure. The agents may be first admixed at the time of contact with the red blood cells or prior to that time.

According to the present invention, red blood cells may be loaded either prior to, simultaneously with, or after the sensitization procedure. In one embodiment of the present invention, the red blood cells may be pre-loaded with the desired agent, and subsequently electrosensitized. In this embodiment, the loading may be performed by any desired technique. If they are loaded and sensitized substantially simultaneously, they may be loaded and sensitized by the same technique. Alternatively, the red blood cells may be sensitized and subsequently loaded. By way of example, the red blood cell may be sensitized by electrosensitization, and loaded using osmotic shock or using electroporation. If more than one agent is employed, the same or a different technique may be used to load the second agent into the red blood cell. In general, if loading is subsequent to sensitization, two or more agents can be loaded in any order. If loading is simultaneous, two or more agents can be admixed prior to contact with the red blood cells or can be added separately, prior to or after the application of the loading procedure mediates uptake of the agents by the cell.

As used herein, the term "substantially simultaneous" means that the site and time of loading and sensitization are such that the loading and sensitization are achieved at approximately the same time.

Preferably the red blood cells of the present invention are sensitized and loaded (in any order) in vitro or ex-vivo.

Preferably the loading is performed by a procedure selected from the group consisting of electroporation, sonoporation, microinjection, calcium precipitation, membrane intercalation, microparticle bombardment, lipid-mediated transfection, viral infection, osmosis, osmotic pulsing, osmotic shock, diffusion, endocytosis, phagocytosis, crosslinking to a red blood cell surface component, chemical crosslinking, mechanical perforation/restoration of the plasma membrane by shearing, single-cell injection or a combination thereof. Sonoporation as a method for loading an agent into a cell is disclosed in, for example, Miller et al (1998), *Ultrasonics* 36, 947–952.

In a preferred aspect of the present invention, the loading procedure is carried out by iontophoresis.

Iontophoresis uses electrical current to activate and to modulate the diffusion of a charged molecule across a biological membrane, such as the skin, in a manner similar to passive diffusion under a concentration gradient, but at a facilitated rate. In general, iontophoresis technology uses an electrical potential or current across a semipermeable barrier. By way of example, delivery of heparin molecules to patients has been shown using iontophoresis, a technique which uses low current (d.c.) to drive charged species into the arterial wall. The iontophoresis technology and references relating thereto is disclosed in WO 97/49450.

In a further preferred aspect of the present invention, loading is carried out by an osmotic shock procedure.

In more detail, the "osmotic shock" mechanism is taught in U.S. Pat. No. 4,478,824. That method involves incubating a packed red blood cell fraction in a solution containing a compound (such as dimethyl sulphoxide (DMSO) or glycerol) which readily diffuses into and out of cells, rapidly creating a transmembrane osmotic gradient by diluting the suspension of red blood cell in the solution with a near-isotonic aqueous medium. This medium contains an anionic agent to be introduced (such as a phosphorylated inositol) which may be an allosteric effect or of hemoglobin, thereby causing diffusion of water into the cells with consequent swelling thereof and increase in permeability of the outer membranes of the cells. This increase in permeability is maintained for a period of time sufficient only to permit transport of the anionic agent into the cells and diffusion of the readily-diffusing compound out of the cells. This method is of limited effectiveness where the desired agent to be loaded into cells is not anionic, or is anionic or polyanionic but is not present in the near-isotonic aqueous medium in sufficient concentration to cause the needed increase in cell permeability without cell destruction.

U.S. Pat. No. 4,931,276 and WO 91/16080 disclose methods of loading red blood cells with selected agents using an osmotic shock technique. Therefore, these techniques can be used to enable loading of red blood cells in the present invention. In U.S. Pat. No. 4,931,276, a modified osmotic shock technique is provided.

Effective agents which may advantageously be loaded into red blood cells using the modified method provided in U.S. Pat. No. 4,931,276 include peptides, purine analogues, pyrimidine analogues, chemotherapeutic agents and antibiotic agents. These agents frequently present drug delivery problems. Specific compounds include but are not limited to tryptophan, phenylalanine and other water-soluble amino acid compounds. Several derivatives of the unnatural analogues of the nucleic acid bases adenine, guanine, cytosine and thymine are well known as useful therapeutic agents, e.g. 6-mercaptopurine (6MP) and azathioprine, which are commonly used as immunosuppressants and inhibitors of malignant cell growth, and azidothymidine (AZT) and analogues thereof which are useful as anti-viral agents, particularly in the treatment of AIDS. It has been shown that the action of these unnatural base derivatives is dependent on intra-cellular conversion thereof to phosphorylated forms (Chan et al., 1987, Pharmacotherapy, 7: 165;14 177; also Mitsuya et al., 1986, Proc. Natl. Acad. Sci. U.S.A., 83: 1911–1915).

An alternative osmotic shock procedure is described in U.S. Pat. No. 4,931,276 which is incorporated herein by reference.

In an advantageous aspect of the present invention, loading is carried out by a microparticle bombardment procedure.

Microparticle bombardment entails coating gold particles with the agent to be loaded, dusting the particles onto a 22 calibre bullet, and firing the bullet into a restraining shield made of a bullet-proof material and having a hole smaller than the diameter of the bullet, such that the gold particles continue in motion toward cells in vitro and, upon contacting these cells, perforate them and deliver the payload to the cell cytoplasm.

It will be appreciated by one skilled in the art that combinations of methods may be used to facilitate the loading of a red blood cell with agents of interest according to the invention. Likewise, it will be appreciated that a first and second agent, may be loaded concurrently or sequentially, in either order, into a red blood cell in any method of the present invention.

As would be apparent to one of skill in the art, any one or more of the above techniques can be used to load red blood cells for use in the invention, either prior to, simultaneously with, separate from or in sequence to the sensitization procedure. For example, U.S. Pat. No. 4,224,313 discloses a process for preparing a mass of loaded cells suspended in a solution by increasing the permeability of the cell membranes by osmotic pressure or an electric field, or both, loading agents by passage from a solution through the membranes of increased permeability, restoring the original permeability by sealing the membranes by regeneration effect, and separating the cells from the solution in which they were suspended. In that procedure, the agents in solution which are to be loaded include i) a pharmaceutical substance which reacts chemically or physically with substances in the extracellular milieu and which, when loaded into the cell, would prematurely destroy the cell membranes, and ii) at least one blood-compatible sugar and protein capable of providing hydrogen bridge bonding- or of entering into covalent bonds with the pharmaceutical substance, thereby inhibiting the reaction of the pharmaceutical substance with the cell membranes.

Selective Release using Ultrasound

According to the invention, agents which are loaded into a red blood cell are released from the red blood cell and into their surroundings, in this case at or into the target site, tissue or cell, by the application of ultrasound directed at a target site, tissue and/or cell.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz'. (From Ultrasonics in clinical diagnosis. Edited by PNT Wells, 2nd. Edition, Publ. Churchill Livingstone [Edinburgh, London & NY, 1977]. The term "ultrasound" includes diagnostic, therapeutic and focused ultrasound. Diagnostic ultrasound refers to an ultrasound energy source in a range up to about 100 mW/cm$^2$ (FDA recommendation). Therapeutic ultrasound refers to an ultrasound energy source in a range up to about 3–4 W/cm$^2$ (WHO recommendation).

Focused ultrasound (FUS) allows thermal energy to be delivered without an invasive probe (see Morocz et al 1998 Journal of Magnetic Resonance Imaging Vol. 8, No. 1, pp. 136–142. Another form of focused ultrasound is high intensity focused ultrasound (HIFU) which is reviewed by Moussatov et al in ULTRASONICS 1998 Vol. 36, No. 8, pp. 893–900 and TranHuuHue et al in ACUSTICA, 1997, Vol. 83, No. 6, pp. 1103–1106.

Preferably, a combination of diagnostic ultrasound and a therapeutic ultrasound is employed.

Preferably the ultrasound is applied to a target cell or target tissue with sufficient strength to disrupt loaded and sensitized red blood cells but without damaging the target tissue or surrounding tissues. In the context of the present invention, the term "damage or damaging" does not include a transient permeabilization of the target site by the ultrasound energy source. Such a permeabilization may facilitate uptake of the released payload at the target site.

Preferably the exposure to an ultrasound energy source is at a power density of from about 0.05 to about 100 Wcm$^{-2}$.

Even more preferably, the exposure to an ultrasound energy source is at a power density of from about 1 to about 15 Wcm$^{-2}$.

Preferably the exposure to an ultrasound energy source is at a frequency of from about 0.015 to about 10.0 MHz.

Preferably the exposure to an ultrasound energy source is at a frequency of from about 0.02 to about 5.0 MHz.

Preferably the exposure is for periods of from about 10 milliseconds to about 60 minutes.

Preferably the exposure is for periods of from about 1 second to about 5 minutes.

Particularly preferably the patient is exposed to an ultrasound energy source at an acoustic power density of from about 0.05 Wcm$^{-2}$ to about 10 Wcm$^{-2}$ with a frequency ranging from about 0.015 to about 10 MHz (see WO 98/52609). However, alternatives are also possible, for example, exposure to an ultrasound energy source at an acoustic power density of above 100 Wcm$^{-2}$, but for reduced periods of time, for example, 1000 Wcm$^{-2}$ for periods in the millisecond range or less.

Use of ultrasound is advantageous as, like light, it can be focused accurately on a target. Moreover, ultrasound is advantageous as it has a broader degree of three-dimensional focus than a light energy source and is better suited to whole-tissue penetration (such as but not limited to a lobe of the liver) or whole organ (such as but not limited to the entire liver or an entire muscle, such as the heart) delivery of agents according to the present invention. In addition, ultrasound may induce a transient permeabilization of the target site so that uptake of a released payload is facilitated at the target site. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In methods of the invention, release of the agent is effected by exposure of red blood cells either in vitro or ex-vivo to an effective amount of a diagnostic ultrasound energy source or a therapeutic ultrasound energy source as described in U.S. Pat. No. 5,558,092 and WO94/28873. The agent, which is released from a red blood cell for use in the present invention may be referred to as the "payload" of that cell. The term "payload" does not refer to the naturally-occurring contents of a red blood cell.

Preferably the agent is released from the red blood cell by treatment of a target site, tissue or cell with ultrasound.

"Release" is not intended to require complete release of the agent from the red blood cell or red blood cell vector, i.e, that all of the agent physically separates from the red blood cell or cellular particles, or that all of the red blood cells that carry the agent are disrupted. Substantial or selective release, as described by this invention, refers to release of the agent at an appropriate location at a concentration and amount acceptable and consistent with achieving the goals of this invention. The selective release of the agent at the target site can be determined by observing among other things, a) the amount which has been released at the target site, tissue or cell and b) its effect on the target site, tissue or cell, the latter determining whether its delivery should increase, decrease or be discontinued.

Blood Cells

In one embodiment of the present invention, the red blood cells which may be loaded and administered to a vertebrate according to the invention are ideally obtained from the intended recipient individual prior to the procedure so as-to ensure complete immunocompatibility. Alternatively, cells are obtained from a second individual of the same species as the recipient; in such a case, the second individual must share the blood type of the intended recipient or must have an immuno-neutral blood type, such as type O in humans. Alternatively, the red blood cell may have its immunological determinants masked by a substance such as PEG (see below).

As used herein, the term "red blood cell" refers to a living red blood cell from an animal. More specifically, the invention contemplates a living, enucleate red blood cell (i.e., a mature erythrocyte) of a vertebrate.

Preferably the red blood cell is a mammalian red blood cell, advantageously a human red blood cell. As used herein, the term "mammal" refers to a member of the class Mammalia including, but not limited to, a rodent, lagomorph, pig or primate. Preferably, the mammal is a human.

As used herein the term "introducing" includes but is not limited to the administration of a red blood cell and/or an agent into a vertebrate.

As used herein in reference to administration of an agent to a vertebrate, the term "introducing" includes but is not limited to causing the agent to enter the circulatory system of the vertebrate by transfusion or to infusing an agent to a target site. It is contemplated that a hollow needle, such as a hypodermic needle or cannula, is inserted through the wall of a blood vessel (e.g., a vein or artery) and the red blood cell is either injected using applied pressure or allowed to diffuse or otherwise migrate into the blood vessel. It is understood that the diameter of the needle is sufficiently large and the pressure sufficiently light to avoid damage of the cell by shear forces. Preferably, introduction of a red blood cell into a vertebrate in a method of the invention is intra-arterial or intravenous. Methods of blood cell transfusion are well known in the art.

Immunocompatibility

"Immunocompatibility" as used in this invention is intended to be interpreted broadly. It contemplates both the activation or inhibition of an immune response, whether that response is humoral, or cell mediated, or otherwise. It is fuller intended to refer to generalized interactions with immune cells or immune receptors irrespective of whether an immune response is generated from the interaction.

It will be apparent to one skilled in the art that it may be desirable to affect the immunocompatibility of the sensitized red blood cells described by this invention. This would be particularly contemplated when said cells are intended to be used in the treatment of disease or delivery or an agent to a site in the animal, or to immune cells themselves. It is contemplated that this may involve rendering the red blood cell more immunogenic so that, for example, the effects of the agent can be enhanced by, or affect or initiate an immune response in an animal. It is also contemplated that it may be desirable to render said red blood cell less immunogenic so that, by example, said sensitized red blood cells or agents they further comprise, do not provoke, or are not sequestered by the immune system. Methods of affecting and compositions for immunoregulation in an animal are well described in the art, and their selection and use will be apparent to one skilled in the art. By way of non-limiting example, the following approaches are specifically contemplated for reducing the immunogenicity of the sensitized red blood cell as contemplated by this invention.

The loaded red blood cell vehicles may be coated with an agent which masks cell surface antigens. For example, PEGylated red blood cells evade the host immune response and thereby enjoy prolonged circulation. According to one such method, methoxy (polyethylene glycol), or mPEG, is covalently bound to red blood cells (Scott et al., 1997, Proc. Natl. Acad. Sci. U.S.A., 94: 7566–7571). This procedure has been shown to result in a loss of ABO blood group reactivity and inhibition of phagocytic destruction by monocytes; in addition, the survival of mPEG treated sheep red blood cells transfused into mice is increased 360-fold over that of untreated control cells (Scott et al., 1997, supra).

A second coating which may be useful in the invention is one which comprises distearoyl-phosphatidylethanolamine (DSPE)-conjugated PEG (Du et al., 1997, Biochim. Biophys. Acta-Biomembranes, 1326: 236–248). When applied as a monolayer film to a glass plate, DSPE-PEG inhibits protein adsorption and cell adhesion to the glass plate (Du et al., 1997, supra).

Targeting

According to a method disclosed in U.S. Pat. No. 4,669,481, limited targeting of red blood cells to a small subset of vertebrate tissues is achieved, if desired, as follows: Treating the red blood cell under mild heating conditions will damage the cells, resulting in rapid sequestration by the reticuloendothelial system. The cells can be specifically targeted for the spleen by heating for 10 minutes at 49° C. Greater temperature or length of heating produces increased cell damage, with resultant hepatic uptake. Thus, if desired, payload delivery to the spleen or liver can be preferentially enhanced; however, the degree to which the payload is lost from damaged cells prior to administration is not known.

As used herein, the term "target" is used in reference to the spatial coordinates (anatomical location) of the cell, tissue or site (such as a vessel) to which the agent of the present invention is delivered. It may also refer to a cell or tissue type. The red blood cells of the invention may be targeted to any desired site in an animal, vertebrate, or mammal. As used herein, the term "site" refers to a region of the body of a vertebrate, which region may comprise an anatomical area, a tissue, a group of tissues, a cell, a group of cells or even substantially all of the cells of the vertebrate.

Preferably the target is a cell.

As used herein, the term "cell" refers to a viable, naturally-occurring or genetically engineered, single unit of an organism.

Preferably the target is a tissue.

As used herein, the term "tissue" refers to a population or physical aggregation of cells within an organism, wherein the cells are of the same cell type or are of cell different types resident within a single organ or other functional unit. As used herein, the term "tissue" refers to intact tissue or tissue fragments, such that the cells are sufficiently aggregated (associated) so as to form a cohesive mass. Alternatively, the term "tissue" refers to a collection of individual cells, such as those which circulate (e.g., in blood or lymphatic fluid) within the vertebrate. A tissue may comprise an entire organ (e.g. the pancreas, the thyroid, a muscle, bone or others) or other system (e.g. the lymphatic system) or a subset of the cells thereof; therefore, a tissue may comprise 0.1–10%, 20–50% or 50–100% of the organ or system (e.g., as is true of islets of the pancreas).

Preferably the target is a vessel.

As used herein the term "vessel" means any artery, vein or other "lumen" in an organism to which ultrasound can be applied and to and an agent may be delivered. A lumen is a channel within a tube or tubular organ. Examples of preferred vessels in the method of the present invention include but are not limited to the coronary artery, carotid artery, the femoral artery, and the iliac artery.

In one embodiment of the present invention, an ultrasound energy source may be focused at the target cell, tissue or site (such as a vessel) as loaded red blood cells circulate through it. For example, a diagnostic and/or therapeutic ultrasound energy source or a combination thereof may be applied to a target tissue. This is particularly applicable to target tissues located on the surface of the subject vertebrate, although deep targets may also be treated with an ultrasound energy source.

Agent

As used herein, the term "agent" includes but is not limited to an atom or molecule, wherein a molecule may be inorganic or organic, a biological effector molecule and/or a nucleic acid encoding an agent such as a biological effector molecule, a protein, a polypeptide, a peptide, a nucleic acid, a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid and a carbohydrate. An agent may be in solution or in suspension (e.g., in crystalline, colloidal or other particulate form). The agent may be in the form of a monomer, dimer, oligomer, etc, or otherwise in a complex. The term "agent" further contemplates regions of an agent which display alone or in combination, biological activity, e.g., the active site of an enzyme, or active domains of a protein, or functional groups of a molecule, or any combination of the above.

The agent may comprise an imaging agent or region thereof, by which term is meant an agent which may be detected, whether in vitro in the context of a tissue, organ or organism in which the agent is located. The imaging agent may emit a detectable signal, such as light or other electromagnetic radiation. The imaging agent may be a radioisotope as known in the art, for example $^{32}P$ or $^{35}S$ or $^{99}Tc$, or a molecule such as a nucleic acid, polypeptide, or other molecule as explained below conjugated with such a radioisotope. The imaging agent may be opaque to radiation, such as X-ray radiation. The imaging agent may also comprise a targeting means by which it is directed to a particular cell, tissue, organ or other compartment within the body of an animal. For example, the agent may comprise a radiolabelled antibody specific for defined molecules, tissues or cells in an organism.

The imaging agent may be combined with, conjugated to, mixed with or combined with, any of the agents disclosed herein. Combinations of agents with multiple or overlapping specificities or utilities are clearly contemplated by this invention.

It will be appreciated that it is not necessary for a single agent to be used, and that it is possible to load two or more agents for into the vehicle. Accordingly, the term "agent" also includes mixtures, fusions, combinations and conjugates, of atoms, molecules etc as disclosed herein. For example, an agent may include but is not limited to: a nucleic acid combined with a polypeptide; two or more polypeptides conjugated to each other; a protein conjugated to a biologically active molecule (which may be a small molecule such as a pro-drug); or a combination of a biologically active molecule with an imaging agent.

As used herein, the term "biological effector molecule" or "biologically active molecule" refers to an agent that has activity in a biological system, including, but not limited to, a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof may be natural, synthetic or humanized, a peptide hormone, a receptor, a signaling molecule or other protein; a nucleic acid, as defined below, including, but not limited to, an oligonucleotide or modified oligonucleotide, an antisense oligonucleotide or modified antisense oligonucleotide, cDNA, genomic DNA, an artificial or natural chromosome (e.g. a yeast artificial chromosome) or a part thereof, RNA, including mRNA, tRNA, rRNA or a ribozyme, or a peptide nucleic acid (PNA); a virus or virus-like particles; a nucleotide or ribonucleotide or synthetic analogue thereof, which may be modified or unmodified; an amino acid or analogue thereof, which may be modified or unmodified; a non-peptide (e.g., steroid) hormone; a proteoglycan; a lipid; or a carbohydrate. If the biological effector molecule is a polypeptide, it may be loaded directly into a red blood cell of the invention; alternatively, a nucleic acid molecule bearing a sequence encoding the polypeptide, which sequence is operatively linked to transcriptional and translational regulatory elements active in a cell at the target site, may be loaded. Small molecules, including inorganic and organic chemicals, are also of use in the present invention. In a particularly preferred embodiment of the invention, the biologically active molecule is a pharmaceutically active agent, for example, an isotope.

Particularly useful classes of biological effector molecules include, but are not limited to, antigens, antibiotics, pro-inflammatory or anti-inflammatory drugs, angiogenic or vasoactive agents, growth factors and cytotoxic agents (e.g., tumor suppressers). Cytotoxic agents of use in the invention include, but are not limited to, diptheria toxin, Pseudomonas exotoxin, cholera toxin, pertussis toxin, and the pro-drugs peptidyl-p-phenylenediamine-mustard, benzoic acid mustard glutamates, ganciclovir, 6-methoxypurine arabinonucleoside (araM), 5-fluorocytosine, glucose, hypoxanthine, methotrexate-alanine, N-[4-(a-D-galactopyranosyl) benyloxycarbonyl]-daunorubicin, amygdalin, azobenzene mustards, glutamyl p-phenylenediamine mustard, phenolmustard-glucuronide, epirubicin-glucuronide, vinca-cephalosporin, phenylenediamine mustard-cephalosporin, nitrogen-mustard-cephalosporin, phenolmustard phosphate, doxorubicin phosphate, mitomycin phosphate, etoposide phosphate, palytoxin-4-hydroxyphenyl-acetamide, doxorubicin-phenoxyacetamide, melphalan-phenoxyacetamide, cyclophosphamide, ifosfamide or analogues thereof. If a pro-drug is loaded in inactive form, a second biological effector molecule may be loaded into the red blood cell of the present invention. Such a second biological effector molecule is usefully an activating polypeptide which converts the inactive pro-drug to active drug form, and which activating polypeptide is selected from the group that includes, but is not limited to, viral thymidine kinase (encoded by Genbank Accession No. J02224), carboxypeptidase A (encoded by Genbank Accession No. M27717), α-galactosidase (encoded by Genbank Accession No. M13571), β-glucuronidase (encoded by Genbank Accession No. M15182), alkaline phosphatase (encoded by Genbank Accession No. J03252 J03512), or cytochrome P-450 (encoded by Genbank Accession No. D00003 N00003), plasmin, carboxypeptidase G2, cytosine deaminase, glucose oxidase, xanthine oxidase, β-glucosidase, azoreductase, t-gutamyl transferase, β-lactamase, or penicillin amidase. Preferably, the polypeptide capable of activating a pro-drug is DT diaphorase. Either the polypeptide or the gene encoding it may be loaded; if the latter, both the pro-drug and the activating polypeptide may be encoded by genes on the same recombinant nucleic acid construct.

Preferably the biological effector molecule is selected from the group consisting of a protein, a polypeptide, a peptide, a nucleic acid, a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid and a carbohydrate or a combination thereof (e.g., chromosomal material comprising both protein and DNA components or a pair or set of effectors, wherein one or more convert another to active form, for example catalytically).

The present invention advantageously employs agents which are not able to diffuse through an intact erythrocyte cell wall by passive or active means. However, the delivery of agents which diffuse at a certain rate through the erythrocyte cell wall is contemplated, particularly where increased delivery of the agent at a particular time or location is desirable. Increased delivery may be achieved by ultrasound administration at the appropriate time or location.

The agents, including biological effector molecules, may also be delivered into cells as fusions (for example, protein or polypeptide fusions) or conjugates with a protein capable of crossing the plasma membrane and/or the nuclear membrane. Preferably, the agent/biological effector molecule is fused or conjugated to a domain or sequence from such a protein responsible for the translocational activity. Preferred translocation domains and sequences include domains and sequences from the HIV-1-trans-activating protein C(at), Drosophila Antennapedia homeodomain protein and the herpes simplex-1 virus VP22 protein. By this means, the agent/biological effector molecule is able to enter the cell or its nucleus when released in the vicinity of the cell using the methods described herein.

Exogenously added HIV-1-trans-activating protein (Tat) can translocate through the plasma membrane and to reach the nucleus to transactivate the viral genome. Translocational activity has been identified in amino acids 37–72 (Fawell et al., 1994, Proc. Natl. Acad. Sci. U.S.A. 91, 664–668), 37–62 (Anderson et al., 1993, Biochem. Biophys. Res. Commun. 194, 876–884) and 49–58 (having the basic sequence RKKRRQRRR (SEQ ID NO: 1)) of HIV-Tat. Vives, et al. (1997), J Biol Chem 272, 16010–7 identified a sequence consisting of amino acids 48–60 (CGRKKRRQRRRPPQC (SEQ ID NO:2)), which appears to be important for translocation, nuclear localization and trans-activation of cellular genes. Intraperitoneal injection of a fusion protein consisting of β-galactosidase and a HIV-TAT protein transduction domain results in delivery of the biologically active fusion protein to all tissues in mice (Schwarze et al., 1999, Science 285, 1569–72).

The third helix of the Drosophila Antennapedia homeodomain protein has also been shown to possess similar properties (reviewed in Prochiantz, A., 1999, Ann N Y Acad Sci, 886, 172–9). The domain responsible for translocation in Antennapedia has been localized to a 16 amino acid long peptide rich in basic amino acids having the sequence RQIKIWFQNRRMKWKK (SEQ ID NO:3); (Derossi, et al., 1994, J Biol Chem, 269, 10444–50). This peptide has been used to direct biologically active substances to the cytoplasm and nucleus of cells in culture (Theodore, et al., 1995, J Neurosci 15, 7158–7167). Cell internalization of the third helix of the Antennapedia homeodomain appears to be receptor-independent, and it has been suggested that the translocation process involves direct interactions with membrane phospholipids (Derossi et al., 1996, J Biol Chem, 271, 18188–93). The VP22 tegurnent protein of herpes simplex virus is capable of intercellular transport, in which VP22 protein expressed in a subpopulation of cells spreads to other cells in the population (Elliot and O'Hare, 1997, Cell 88, 223–33). Fusion proteins consisting of GFP (Elliott and O'Hare, 1999, Gene Ther 6, 149–51), thymidine kinase protein (Dilber et al., 1999, Gene Ther 6, 12–21) or p53 (Phelan et al., 1998, Nat Biotechnol 16, 440–3) with VP22 have been targeted to cells in this manner.

Particular domains or sequences from proteins capable of translocation through the nuclear and/or plasma membranes may be identified by mutagenesis or deletion studies. Alternatively, synthetic or expressed peptides having candidate sequences may be linked to reporters and translocation assayed. For example, synthetic peptides may be conjugated to fluoroscein and translocation monitored by fluorescence microscopy by methods described in Vives et al. (1997), J Biol Chem 272, 16010–7. Alternatively, green fluorescent protein may be used as a reporter (Phelan et al., 1998, Nat Biotechnol 16, 440–3).

Any of the domains or sequences or as set out above or identified as having translocational activity may be used to direct the agents (including biological effector molecules) into the cytoplasm or nucleus of a cell.

Nucleic Acid

A nucleic acid of use in the invention may comprise a viral or non-viral DNA or RNA vector, where non-viral vectors include, but are not limited to, plasmids, linear nucleic acid molecules, artificial chromosomes and episoral vectors. Expression of heterologous genes has been observed after injection of plasmid DNA into muscle (Wolff J. A. et al., 1990, Science, 247: 1465–1468; Carson D. A. et al., U.S. Pat. No. 5,580,859), thyroid (Sykes et al., 1994, Human Gene Ther., 5: 837–844), melanoma (Vile et al., 1993, Cancer Res., 53: 962–967), skin (Hengge et al., 1995, Nature Genet., 10: 161–166), liver (Hickman et al., 1994, Human Gene Therapy, 5: 1477–1483) and after exposure of airway epithelium (Meyer et al., 1995, Gene Therapy, 2: 450–460).

As used herein, the term "nucleic acid" is defined to encompass DNA and RNA or both synthetic and natural origin which DNA or RNA may contain modified or unmodified deoxy- or dideoxy-nucleotides or ribonucleotides or analogues thereof. The nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides. The term "nucleic acid" is also intended to include oligonucleotides and modified oligonucleotides.

The term "synthetic", as used herein, is defined as that which is produced by in vitro chemical or enzymatic synthesis.

Therapeutic nucleic acid sequences useful according to the methods of the invention include those encoding receptors, enzymes, ligands, regulatory factors, and structural proteins. Therapeutic nucleic acid sequences also include sequences encoding nuclear proteins, cytoplasmic proteins, mitochondrial proteins, secreted proteins, plasmalemma-associated proteins, serum proteins, viral antigens, bacterial antigens, protozoal antigens and parasitic antigens. Therapeutic nucleic acid sequences useful according to the invention also include sequences encoding proteins, lipoproteins, glycoproteins, phosphoproteins and nucleic acids (e.g., RNAs such as ribozymes or antisense nucleic acids). Ribozymes of the hammerhead class are the smallest known, and lend themselves both to in vitro synthesis and delivery to cells (summarized by Sullivan, 1994, J. Invest. Dermatol., 103: 85S–98S; Usman et al., 1996, Curr. Opin. Struct. Biol., 6: 527–533). Proteins or polypeptides which can be expressed by nucleic acid molecules delivered according to the present invention include hormones, growth factors, neurotransmitters, enzymes, clotting factors, apolipoproteins, receptors, drugs, oncogenes, tumor antigens, tumor suppressers, structural proteins, viral antigens, parasitic antigens and bacterial antigens. The compounds which can be incorporated are only limited by the availability of the nucleic acid sequence encoding a given protein or polypeptide. One skilled in the art will readily recognize that as more proteins and polypeptides become identified, their corresponding genes can be cloned into the gene expression vector(s) of choice, administered to a tissue of a recipient patient or other vertebrate, and expressed in that tissue.

Delivery of Agents

The method of the present invention is useful for the delivery of agents to a selected site in an animal, whether an organ, part of an organ, cell, cell type, or tissue, or otherwise, in the presence or absence of specific targeting means. This is achieved, as set out above, by the selective disruption by ultrasound at the selected target site of electrosensitized red blood cells loaded with the agent of choice.

Agents useful for use in the present invention are set out above. Preferred agents include those useful for imaging of tissues in vivo or ex vivo. For example, imaging agents, such as labeled antibodies which are specific for defined molecules, tissues or cells in an organism, may be used to image specific parts of the body by releasing them at a desired location using ultrasound. This allows imaging agents which are not completely specific for the desired target, and which might otherwise lead to more general imaging throughout the organism, to be used to image defined tissues or structures. For example, an antibody which is capable of imaging endothelial tissue may be used to image liver vasculature by releasing the antibody selectively in the liver by applying ultrasound thereto.

Kits

The invention also encompasses a kit comprising a red blood cell, an agent and packaging materials therefor.

A kit designed for the easy delivery of an agent to a recipient vertebrate, whether in a research of clinical setting, is encompassed by the present invention. A kit takes one of several forms, as follows:

A kit for the delivery of an agent to a subject vertebrate comprises red blood cells and the agent and instructions for performing the method of the present invention. Alternatively, the red blood cells are supplied loaded with the agent for convenience of use by the purchaser. The cells are supplied sensitized for rapid use or, for greater stability, unsensitized. In the latter case, the sensitizing process is carried out separately from the cells. The cells of the kit are species-specific to the vertebrate of interest, such as a primate, including a human, canine, rodent, pig or other, as desired; in other words, the cells are of like species with the intended recipient. The cells of the kit are, additionally, specific to the blood type of the intended recipient organism, as needed. Optionally, the kit comprises one or more buffers for cell sensitization, washing, resuspension, dilution and/or administration to a vertebrate. Appropriate buffers are selected from the group that includes low ionic strength saline, physiological buffers such as PBS or Ringer's solution, cell culture medium and blood plasma or lymphatic fluid. The kit additionally comprises packaging materials (such as tubes, vials, bottles, or sealed bags or pouches) for each individual component and an outer packaging, such as a box, canister or cooler, which contains all of the components of the kit. The kit is shipped refrigerated. Optionally, non-cellular components are supplied at room temperature or frozen, as needed to maintain their activity during storage and shipping. They may be in liquid or dry (i.e., powder) form.

A second kit of the invention comprises an agent such as a biological effector molecule, instructions for performing the method of the present invention and, optionally a sensitizing device and buffers therefor (e.g., saline or other physiological salt buffer, culture medium, plasma or lymphatic fluid). In addition, the kit contains appropriate packaging materials, as described above. The individual components may be supplied in liquid or dry (i.e., powder) form, and may be at room temperature, refrigerated or frozen as needed to maintain their activity during storage and shipping. Red blood cells for use with this kit are obtained independently (for example, they may be harvested from the intended recipient vertebrate).

A preferred aspect of the invention is a kit comprising a red blood cell which is loaded with an agent, and packaging materials therefor.

Preferably, a kit as described above further comprises an apparatus for applying the sensitizing procedure.

Preferably the kit further comprises polyethylene glycol.

It is additionally preferred that the kit further comprises a liquid selected from the group consisting of a buffer, diluent or other excipient.

Preferably, the liquid is selected from the group consisting of a saline buffer, a physiological buffer and plasma. A final aspect of the invention is a physiological composition comprising a red blood cell comprising a biological effector molecule admixed with a physiologically compatible buffer. As used herein, the term "physiologically compatible buffer" or "physiological buffer" is defined as a liquid composition which, when placed in contact with living cells, permits the cells to remain alive over a period of minutes, hours or days. As such, a physiological buffer is substantially isotonic with the cell, such that cell volume does not change more than 20% due to differences in internal and external ionic strength. Non-limiting examples of physiologically compatible buffers or physiological buffers include dilute saline, which may be buffered (e.g., Hanks' buffered saline or phosphate buffered saline), or other physiological salts (e.g., Ringer's solution), dilute glucose, sucrose or other sugar, dilute glycerol with- or without salts or sugars, cell culture media as are known in the art, serum and plasma.

Preferably, the red blood cell of the physiological composition is human.

EXAMPLES

Example 1

Electric field-mediated sensitivity of human red blood cells and polyethylene glycol (PEG)-treated red blood cells to ultrasound in PBS/Mg/glucose buffer The responses of normal cells were compared with those of electroporated and re-sealed cells following exposure to ultrasound over a range of power densities. The responses of normal cells were also compared with those of polyethylene glycol (PEG) treated cells which had been electroporated and re-sealed under similar conditions. To this end human blood was harvested by venipuncture and washed twice in PBS (phosphate buffered saline) by centrifugation. Cells were suspended in PBS containing 1 mg/ml fluorescein to yield concentrations of $7 \times 10^8$ cells/ml and 0.8 ml aliquots were dispensed into electroporation cuvettes (0.4 cm electrode gap) and retained on ice for 10 min. Cells were then exposed to an electroporation strategy involving delivery of two electric pulses (field strength=3.625 kV/cm at a capacitance of 1 $\mu$F) using a BioRad Gene Pulser apparatus. Cells were immediately washed with PBS containing $MgCl_2$ (4 mM) (PBS/Mg) and retained at room temperature for 30 min. in the PBS/Mg (containing 1 mg/ml fluorescein) buffer to facilitate re-sealing. Aliquots of those cells were treated with polyethylene glycol (av. mol. Weight=5000) as described by Scott et al., 1997 Proc. Natl. Acad. Sci. (U.S.A.), 94, 7566–7571 using cyanuric chloride treated methoxy polyethylene glycol at a concentration of 25 mg/ml. Cells were subsequently washed and suspended at a concentration of $14 \times 10^8$ cells/ml in PBS/Mg containing 10 mM glucose (PBS/Mg/glucose) for at least 1 hour. Samples were treated with ultrasound by dispensing 0.1 ml aliquots of cells into microwells (inner diameter=5 mm). Ultrasound power densities were generated using a Rich-Mar Multi Hz generator fitted with a 3 MHz ultrasound head (U.S.A.) and set to delivery continuous wave ultrasound at the required power density. Samples were treated for 30 seconds and cell counts were subsequently determined using a hemocytometer. In addition, samples of cells were analyzed using a Becton Dickinson flow cytometer in order to determine leakage of fluorescein following exposure to ultrasound.

Results 1

The results are shown in FIG. 1 and they demonstrate that the ultrasound power densities between 0.5 and 1.5 W/cm$^2$ had little or not effect on either normal or PEG-treated red blood cells. However, when electroporated normal and PEG-treated cells were exposed to increasing ultrasound power densities very significant lysis was detected, particularly at densities above 1 W/cm$^2$. The results demonstrate that cells which had been treated using conditions suitable for electroporative loading of materials into human red blood cells were rendered hyper-sensitive to ultrasound during that loading procedure. In addition to examining cell lysis it was also decided to employ flow cytometry to determine whether or not the pay-load was released during exposure to ultrasound. Again the results are shown in FIG. 1 and it was found that when PEG-treated cells loaded with fluorescein were exposed to increasing ultrasound power densities the geometric mean of fluorescence decreased. The control population for this experiment consisted of PEG-treated cells which were exposed to fluorescein in the absence of exposure to electric field conditions. The results demonstrate ultrasound-mediated leakage of a pay-load from the hyper-sensitized, PEG-treated red blood cells.

Example 2

Electric field-mediated sensitivity of human red blood cell and polyethylene glycol-treated red blood cells to ultrasound in autologous plasma The data in Example 1 demonstrated that cells which had been treated with electric field conditions suitable for loading human red blood cells were rendered hyper-sensitive to ultrasound. This degree of sensitivity remained following storage of the samples for 1 hour in PBS/Mg/glucose buffer. It was of interest to determine whether or not the electrosensitized cells exhibited sensitivity to ultrasound in the presence of autologous plasma. To this end both normal and PEG-treated human red blood cells were electrosensitized in the presence of fluorescein as described for Example 1. Cells were allowed to re-seal in PBS/Mg (containing fluorescein) for 30 min. and subsequently placed in PBS/Mg/glucose for 15 min. Cells were then suspended in to autologous plasma at a concentration of approximately $14 \times 10^8$ cell/ml. Cells were stored at room temperature for 1 hour and then treated with ultrasound at the indicated power densities and cell counts determined as described for Example 1. In addition, samples of cells were analyzed using a Becton Dickinson flow cytometer in order to determine leakage of fluorescein following exposure to ultrasound.

Results 2

Figure 2A:
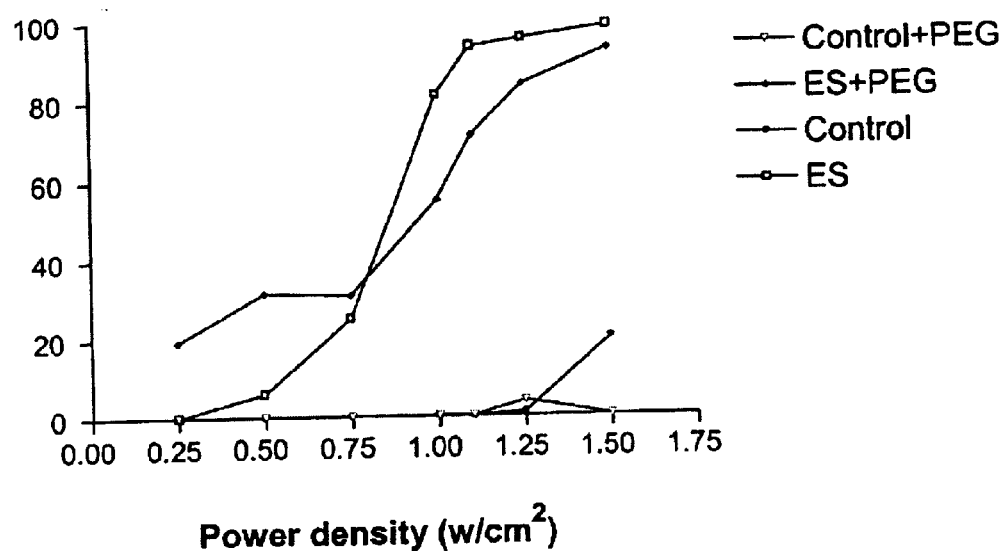
FIG. 2A shows the effect of ultrasound power density on control normal (●), control PEG-treated (▼), electro-sensitised (□) and electro-sensitised, PEG-treated (♦) human red blood cells in autologous plasma X-axis: power density (W/cm$^2$); Y-axis: % lysis.
Figure 2B:
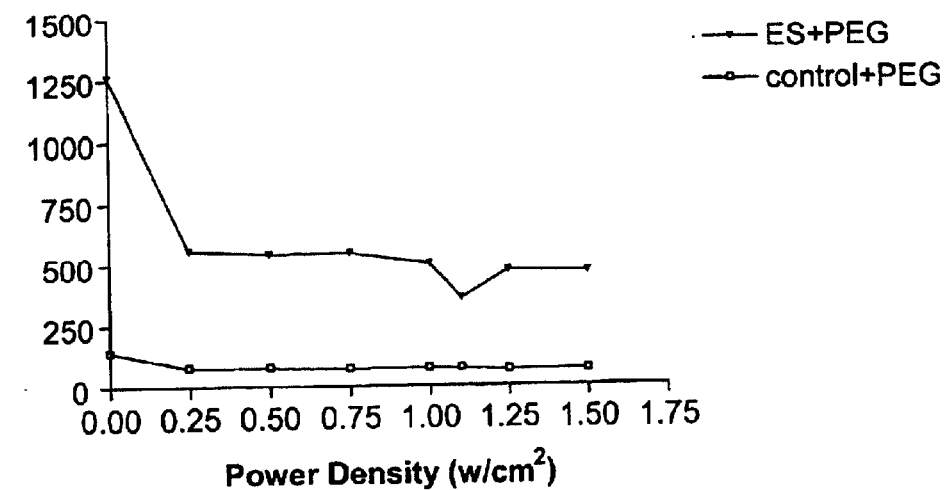
FIG. 2B shows the geometric mean of fluorescence from populations of PEG-treated control (□) and electro-sensitised PEG-treated (▼) human red blood cells exposed to each power density and determined using flow cytometry. X-axis: power density (W/cm$^2$); Y-axis: geometric mean.

The results are shown in FIG. 2A and they demonstrate that exposing normal and PEG-treated control cell populations in the presence of plasma to ultrasound has little or not effect on those cells at power densities ranging from 0.25–1.5 W/cm$^2$. However, exposure of the electrosensitized normal and PEG-treated cells to ultrasound in the presence of plasma results in increasing cell lysis with increasing power density (FIG. 2A). These results demonstrate that the susceptibility of both electrosensitized human red blood cells and PEG-treated human red blood cells to ultrasound remains in the presence of autologous plasma. In addition, it was found that ultrasound-mediated release of the loaded fluorescein was achieved following exposure of the electrosensitized, PEG-treated cells to increasing power densities as demonstrated by a decrease in the geometric mean of fluorescence using flow cytometry (FIG. 2B). Control populations of cells consisted of exposing PEG-treated cells exposed to fluorescein in the absence of an electosensitization event (FIG. 2B). These results demonstrate ultrasound-mediated leakage of a pay-load from the hyper-sensitized, PEG-treated red blood cells in the presence of autologous plasma.

Example 3

Stability of electric field-mediated sensitization of normal and PEG-treated human red blood cells to ultrasound during prolonged storage in PBS/Mg/Glucose Examples 1 and 2 demonstrated that exposure of both normal and PEG-treated red blood cells to electric field conditions suitable for loading cells coincidentally conferred upon those cells hyper-sensitivity to ultrasound. It was decided to determine whether or not hyper-sensitivity persisted during storage. Cells were harvested and electrosensitized as described for Example 1. Cells were subsequently re-sealed in PBS/Mg for 30 min. and a proportion were treated with PEG as described by Scott et al. (1997) Proc. Natl. Acad. Sci. (USA), 94, 7566–7571). Cells were then suspended in PBS/Mg/glucose (supplemented with 1% v/v penicillin/ streptomycin solution [5000 IU/ml] and 1% v/v gentamicin [10 mg/ml]) to yield concentrations of $14 \times 10^8$ cells/ml. Cells were stored at 4° c. and samples were treated with ultrasound (1.25 W/cm$^2$ for 30 seconds using a 3 MHz ultrasound head) as described in Example 1. The degree of cell lysis was determined using a hemocytometer.

Results 3

Figure 3:
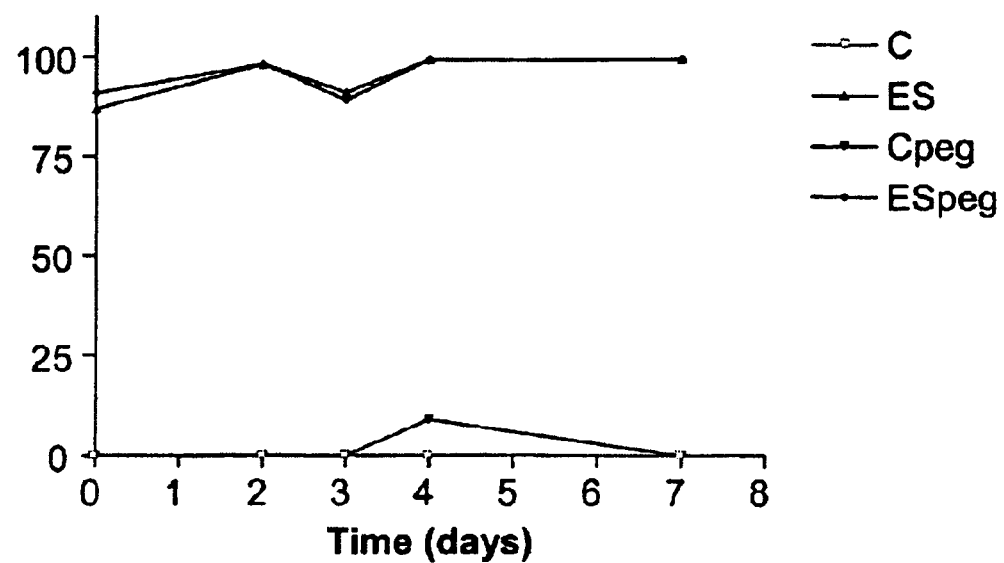
FIG. 3 shows the effect of ultrasound (1.25 W/cm$^2$, 30 seconds) on control normal (■), control PEG-treated (▼), electrosensitized normal (▲) and electrosensitized PEG-(♦) human red blood cells which had been stored for the indicated times at 4° C. in PBS/Mg/glucose. X-axis: time (days); Y-axis: % lysis.

The results are shown in FIG. 3 and they demonstrate that both normal and PEG-treated cells exhibit little or no susceptibility to ultrasound during storage over a 7 day period. The results also demonstrate that the degree of ultrasound sensitivity induced by electrosensitization in both red blood cells and PEG-treated red blood cells is retained over this period of time. It was concluded from this experiment that the electrosensitization phenomenon exhibited by both the red blood cells and the PEG-treated red blood cells is retained during storage at 4° C. in PBS/Mg/glucose.

Example 4

Stability of electric field-mediated sensitization of normal and PEG-treated human red blood cells to ultrasound during storage in autologous plasma It has been shown in Example 3 that cells which had been rendered ultrasound sensitive using electrosensitization remained sensitive for prolonged periods of time during storage on PBS/Mg/glucose. It was of interest to determine whether or not this phenomenon could be retained for prolonged periods of time during storage in autologous plasma To this end both sensitized and non-sensitized normal and PEG-treated cells were prepared as described for Example 3. Samples were re-sealed for 30 min in PBS/Mg and subsequently transferred to PBS/Mg/glucose for 15 min. Cells were then suspended in autologous plasma supplemented with 1% v/v penicillin/streptomycin solution [5000 IU/ml] and 1% v/v gentamicin [10 mg/ml]) to yield concentrations of $13 \times 10^8$ cells/ml. Cells were stored at 4° C. and samples were treated with ultrasound as described in Example 3.

Results 4

Figure 4:
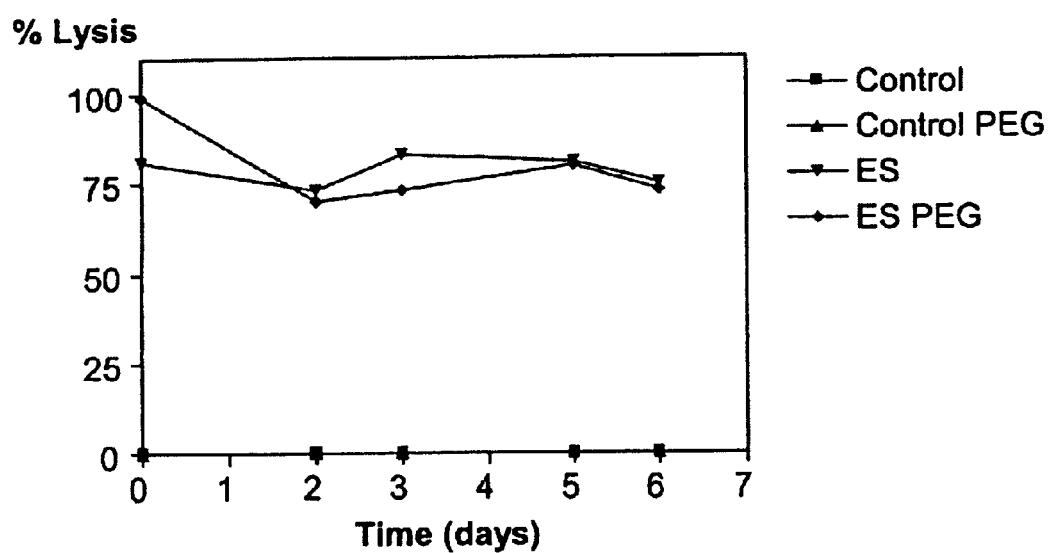
FIG. 4 shows the effect of ultrasound (1.25 W/cm$^2$) on control normal (■), control PEG-treated (▲), electrosensitized normal (▼) and electrosensitized PEG-treated (♦) human red blood cells stored for the indicated times at 4° C. in autologous plasma. X-axis: time (days); Y-axis: % lysis.

The results obtained are shown in FIG. 4 and they demonstrate that normal and PEG-treated red blood cells stored in autologous plasma for 6 days remained insensitive to ultrasound. However, electrosensitized normal and PEG-treated cells exhibited hyper-sensitivity to ultrasound over the time period examined. These results demonstrate that the electrosensitized cells retained their sensitivity even over prolonged periods of time in autologous plasma Example 5

The effect of electroporation conditions on sensitivity of human red blood cells to ultrasound Since the above results demonstrated that exposure of human red blood cells to short duration (0.02 mseconds) double electric pulses of 1.45 kV (3.625 kV/cm) at a capacitance of 1 uF conferred upon those cells sensitivity to lysis by ultrasound it was decided to determine whether or not alternative electric pulse conditions might yield similarly sensitized cells. The wave form of the above pulses is referred to as and exponential and describes decay of the delivered pulse across the electrodes. Alternatives include either a square wave or a modulated wave decay across the electrodes in the electroporation cuvettes. In order to examine a representative range of electrical conditions it was decided to study a number of parameters associated with exponential wave decay. These included pulse number delivered to the cuvettes, the capacitance of the pulse(s) delivered, the voltage of each pulse and the effect of delivering sequential pulses at varying voltages. Cells were suspended at not greater than $7 \times 10^8$ cells/ml in PBS, exposed to the conditions described in Table 1 and finally suspended in PBS/Mg/glucose for at least 1 hour prior to exposure to ultrasound. Conditions for exposure to ultrasound were those described for Example 1. Cell lysis was determined by counting surviving cells. In addition, it was decided to examine the effects of delivering both square wave and modulated wave pulses to cells and to assess such delivery in terms of susceptibility to ultrasound. In these cases cells were exposed to electric pulses in electroporation cuvettes with a 0.2 cm electrode gap. Cells were again suspended in PBS during delivery of pulses and subsequently exposed to ultrasound following suspension in PBS/Mg/glucose for 1 hour. Cell lysis was determined by counting cells remaining after treatment with ultrasound. In all of the above studies control populations of cells, which had not been exposed to electric pulses, were treated with ultrasound and cell lysis was determined by cell counting.

Results 5

The results obtained in this series of studies are shown in Table 1 below and they and a number of features in terms of inducing ultrasound sensitivity are evident: (i) Ultrasound sensitivity may be induced using pulses delivered as exponential, square or modulated wave forms. (ii) Increasing the pulse number using exponential wave delivery increases red blood cell sensitivity to ultrasound at lower voltage (see Table 1; 0.7 kV, 1 uF single and double exponential pulse). (iii) Increasing the capacitance at lower pulse voltages increases the ultrasound sensitivity (Table 1; 0.6 kV, 1 uF). (iv) Sequential delivery of low, high and finally low voltage using exponential wave form results in ultrasound sensitivity. (v) Ultrasound sensitivity may be induced using pulses with exponential, square and modulated wave forms. These results demonstrate that ultrasound sensitivity may be induced using a relatively wide variety of electrical parameters.

TABLE 1

ELECTROPORATION CONDITIONS
SUITABLE FOR SENSITIZATION TO ULTRASOUND

| Conditions U/S sensitivity Exponential wave+ | % cell lysis |
|---|---|
| Single pulse | |
| 0.7 kV, 1 uF | 15 |
| 1 kV, 1 uF | 80 |
| 1.45 kV, 1 uF | 100 |
| Double pulse | |
| 0.7 kV, 1 uF | 84 |
| 1 kV, 1 uF | 88 |
| 1.45 kV, 1 uF | 96 |

TABLE 1-continued

ELECTROPORATION CONDITIONS
SUITABLE FOR SENSITIZATION TO ULTRASOUND

| Conditions U/S sensitivity<br>Exponential wave[+] | % cell lysis |
|---|---|
| Sequential pulsing | |
| 0.3 kV, 10 uF: 1.45 kV, 1 uF: 0.3 kV, 10 uF | 98 |
| Increased capacitance | |
| 0.6 kV, 1 uF | 4 |
| 0.6 kV,10 uF | 86 |
| Using BioRad RF module* (square wave) | |
| 0.1 kV, 40 kHz, 100 ms burst, 1 s burst interval, 5 bursts | |
| 0% modulation (square wave) | 90 |
| 100% modulation | 91 |

[+]All samples were treated in 0.4 cm curvettes and electric pulse conditions were delivered using a BioRad Gene Pulsar apparatus. Voltages refer to those delivered by the apparatus.
*The BioRad RF module is designed to deliver either square wave or modulated wave pulses. In all of the above studies pulses were delivered to cells suspended in PBS. Cells were exposed to ultrasound as described for Example 1 using 1.25 W/cm$^2$ for 30 s. In all cases control populations of cells at the same concentration were exposed to ultrasound. In those control sample no significant lysis was detected following exposure to ultrasound Example 6

Effect of cell concentration on electric field mediated sensitization of human red blood cells to ULTRASOUND.

The purpose of this study was to determine whether increasing the concentration of the electrosensitized cells resulted in decreased responses to ultrasound. In order to determine whether or not this might be the case samples of cells were harvested as described for Example 1 and cell concentrations were adjusted to 8 and 14×10$^8$ cells/ml. Populations were then electroporated, placed in PBS/Mg for 30 minutes to re-seal and subsequently suspended in PBS/Mg/glucose for storage at room temperature. Both populations were stored for 1 h and 3 h prior to treatment with ultrasound as described for Examples above (3 MHz, 1.5 W/cm$^2$, 5 min.) and cell counts were determined 30 min. after treatment. Control samples were treated in a similar manner although the electroporation event was omitted.

Results 6

Figure 5:
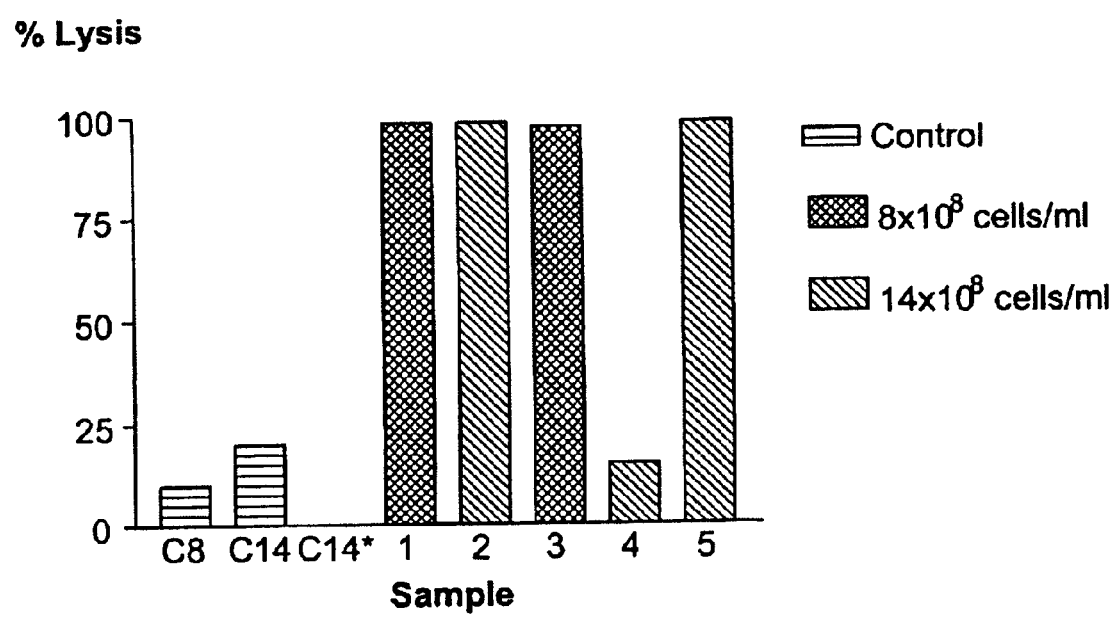
FIG. 5 shows the effect of cell concentration on electrosensitization to ultrasound. Cells were (i) electrosensitized at 8×10$^8$ cells/ml, re-sealed in PBS/Mg, stored in PBS/Mg/glucose for 1 and 3 h and finally subjected to ultrasound (1.5 W/cm$^2$, 3 MHz, 5 min.) (Samples 1 and 3, respectively). Alternatively (ii) cells were electrosensitized at 14×10$^8$ cells/ml and treated in a similar manner before treatment with ultrasound (Samples 2 and 4, respectively). Finally (iii) Sample 5 consisted of cells which were electrosensitized at 8×10$^8$ cells/ml, re-sealed as described above, pooled to 14×10$^8$ cells/ml, stored for 3 h and finally treated with ultrasound. Control samples, C8, C14 and C14* consisted of cells treated in a similar manner to the three sets of cells described above (i, ii, iii, respectively) excluding electrosensitization. X-axis: sample number; Y-axis: % lysis.

The results are shown in FIG. 5 and they indicate little or no effect in control samples (C8 and C14) for both cell concentrations. When cells were stored for 1 h and treated with ultrasound, lysis in both populations was 98–99% (FIG. 5; Samples 1 and 2). However when samples were stored for 3 h and subsequently treated with ultrasound, lysis of the population containing 8×10$^8$ cells/ml was 99% whereas that of the population containing 14×10$^8$ cells/ml was only 15% (FIG. 5; Samples 3 and 4, respectively). These results suggested that cells at the higher concentration had the ability to recover from electrosensitization during storage. Since a higher concentration of cells had been employed in the electrosensitization process it seemed reasonable to presume that electric field-mediated effects on individual cells within the overall population would be reduced. This may have resulted in the ability of those individual cells to recover from sensitization. In order to test this hypothesis, cells were harvested and electroporated in aliquots containing 8×10$^8$ cells/ml. Cells were allowed to recover in PBS/Mg at that concentration for 30 min. and subsequently pooled to yield 14×10$^8$ cells/ml in PBS/Mg/glucose for storage (RT). Cells were treated with ultrasound following 3 h storage and cell counts were determined 30 min. later. Control samples (C14*) were treated in a similar manner without delivery of the electrosensitization pulses. The results are shown in FIG. 5 (Sample 5) and it would found that 99% of the cells lysed following treatment. These results confirmed out hypothesis and demonstrated that in order for ultrasound-sensitivity to persist at higher cell concentrations it would be necessary to perform the electrosensitization procedure at lower cell concentrations. It would alternatively suggest that electrosensitization of human red blood cells at higher cell concentrations would require adjustment of the electrical parameters delivered to those cells in order to sustain ultrasound sensitivity during storage.

Example 7

Effects of ultrasound on electrosensitized human red blood cells placed in a soft tissue phantom The results above demonstrate that electrosensitization of human red blood cells to ultrasound may be achieved in such a manner that those cells may be selectively lysed using ultrasound parameters which have little or no effect on normal human red blood cells in vitro. The purpose of this study was to demonstrate the selective effect in vivo. To this end a soft tissue Doppler phantom was employed (supplied by Dansk Fantom Service, Denmark). The phantom consists of a matrix which transmits sound at a mean velocity of 1503 ms$^{-1}$ at 3 MHz, attenuates sound at 0.54 dB cm$^{-1}$*MHz and has a density of 1040 Kg m$^{-3}$. The system contains tubing with an inner diameter of 1.6 mm and an outer diameter of 3 mm which travels through the matrix at a 25° angle to the scanning surface. Samples of cells (7–8×10$^8$) were injected into the tubing such that each sample treated was at an average depth of 1 cm from the scanning surface. Cells used in the system were harvested, electrosensitized as described above in Example 1, re-sealed in PBS/Mg for 30 min. and subsequently injected into the phantom. Control samples were treated in a similar manner except that electrosensitization was not carried out Samples were treated with the 3 MHz and 1 MHz ultrasound heads for 5 min.

Results 7

Figure 6:
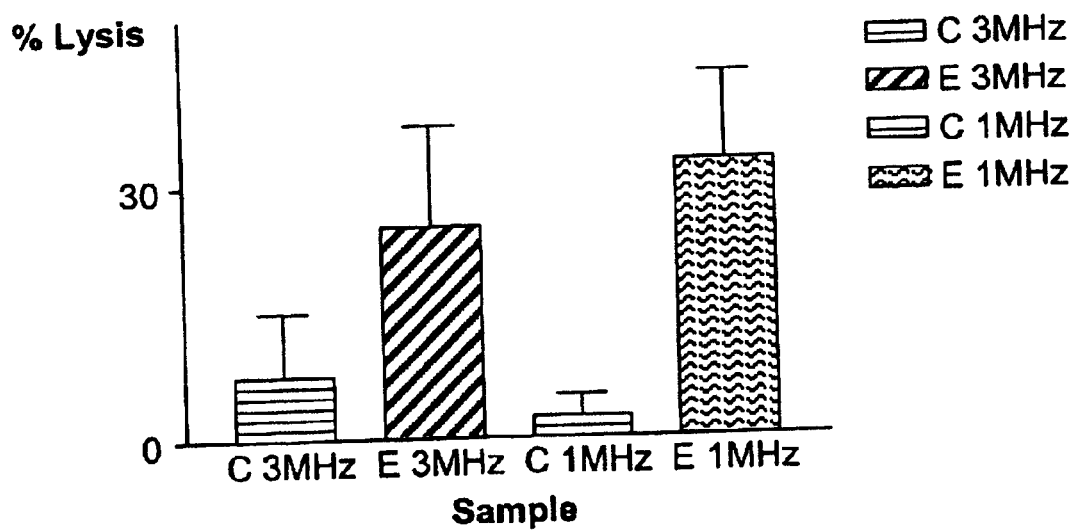
FIG. 6 shows the response of electrosensitized and normal human red blood cells in a soft tissue mimicking phantom system following exposure to 5 min. ULTRASOUND at 1.5 W/cm$^2$ and at 3 and 1 MHz. Cell samples were placed at an average distance of 1 cm from the scanning surface (ultrasound head surface) during treatments. Samples were then retrieved from the system and cell counts were determined using a hemocytometer. X-axis: sample number, Y-axis: % lysis.

The results obtained are shown in FIG. 6 and they demonstrate that at 3 MHz treatment resulted in an average of 7% lysis whereas treatment of the electrosensitized samples resulted in 24% lysis. At 1 MHz treatment resulted in 3% lysis in control samples and 34% lysis in samples which had been electrosensitized. These results demonstrated that preferential lysis of electrosensitized human red blood cells may be achieved in a soft tissue vascular mimicking system. The results suggest that ultrasound could be exploited as a non-invasive means of releasing pay-load from a delivery vehicle which has been electrosensitized.

Example 8

Electrosensitization

To demonstrate that electrosensitization of red blood cells occurs in the absence of electroporation under conditions of insufficient electric field energy to achieve electroporation, an experiment was designed in which a FITC-labeled polyclonal antiserum was loaded into red blood cells by electroporation. Cell lysis in response to ultrasound was assessed on a hemocytometer as in Example 1. The field strength was then reduced was then reduced to a point at which no antibody loading was observed, and cell lysis in response to ultrasound was again assessed.

In a first experiment, 4.5×10⁷ RBCs were incubated with 0.25 mg/ml antibody, cooled to 4° C. and electrosensitized by pulsing at 0.3 KV 10 $\mu$F, 1.45 KV 1 $\mu$F and 0.3 KV 10 $\mu$F in phosphate-buffered sucrose (PBSucrose).

In a second experiment, 3.5×10⁷ RBCs were incubated with 0.25 mg/ml antibody, cooled to 4° C. and electrosensitized by pulsing at 0.3 KV 10 $\mu$F, 1.45 KV 1 $\mu$F and 0.3 KV 10 $\mu$F in PBS.

In a third experiment, 5×10⁷ RBCs were incubated with 0.5 mg/ml antibody, cooled to 4° C. and electrosensitized by pulsing twice at 1.45 KV 1 $\mu$F in PBS.

Results 8

Figure 7A:
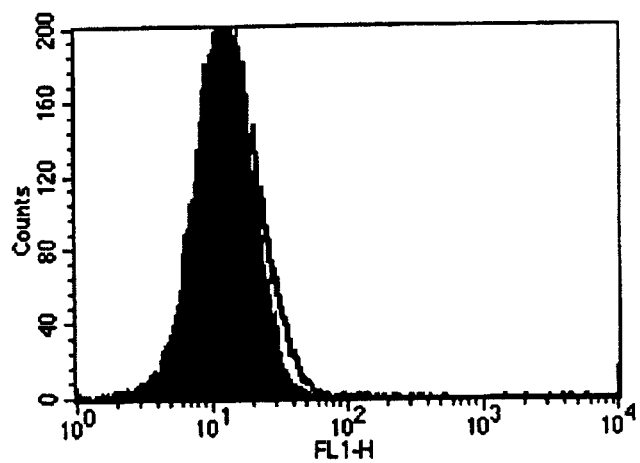
FIG. 7 shows a flow cytometer analysis of cells subjected to loading by electroporation at varying electric field strengths. The filled traces represent cells which have not been electroporated, but exposed to antibody; these traces are overlayed with an open trace, representing cells which have been subjected to electroporation, with the antibody. The conditions are as follows: panel (a) 5×10$^7$ RBC+0.5 mg/ml antibody, pulsing twice at 1.45 KV 1 μF in PBS at 4 degrees C.; panel (b) 3.5×10$^7$ RBC+0.25 mg/ml antibody, pulsing at 0.3 KV 10 μF, 1.45 KV 1 μF and 0.3 KV 10 μF in PBS at 4 degrees C.; pane (c) 4.5×10$^7$ RBC+0.25 mg/ml antibody, pulsing at 0.3 KV 10 μF, 1.45 KV 1 μF and 0.3 KV 10 μF in PBSucrose at 4 degrees C. X-axis: FLH-1; Y-axis: counts.
Figure 7B:
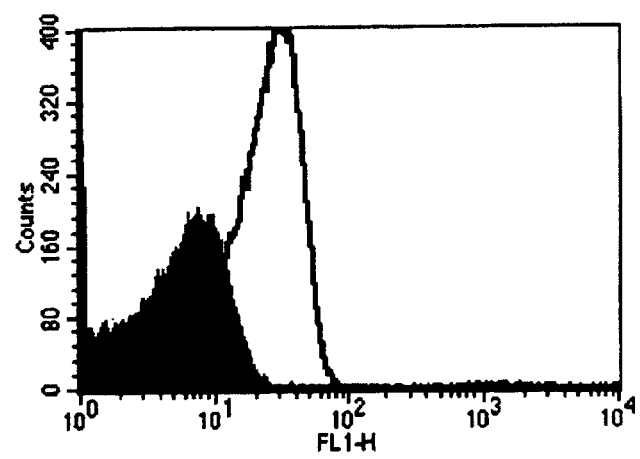
Figure 7C:
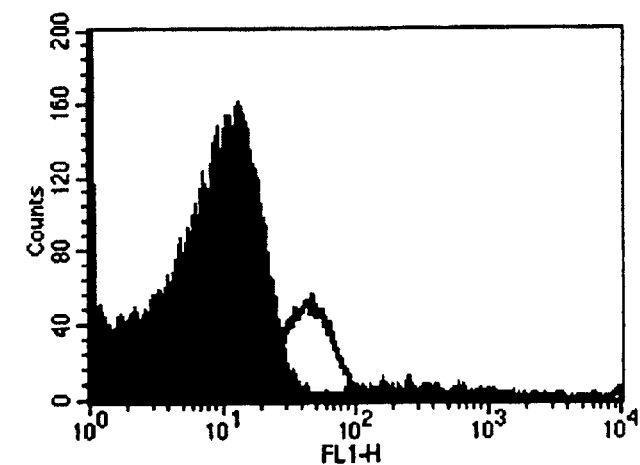

The first and second experiments, pulsing at 0.3 KV 10 $\mu$F, 1.45 KV 1 $\mu$F and 0.3 KV 10 $\mu$F in PBS or PBSucrose, showed antibody loading at ratios of 3.98 and 4.04 respectively as determined by FACS (FIG. 7). The cells were also 100% sensitive to ultrasound as determined by hemocytometer counting, according to Example 1.

The third experiment, pulsing twice at 1.45 KV 1 $\mu$F in PBS, showed no antibody loading when analyzed by FACS (FIG. 7). However, the cells remained 100% sensitive to ultrasound as determined by hemocytometer counting.

Example 9

Electro-sensitization of human red blood cells treated with a hypotonic dialysis loading protocol.

The objective of these experiment was to determine whether or not it would be possible to electrosensitize human red blood cells which may be loaded using alternative loading modalities. It was decided to employ a protocol designed to achieve loading using hypotonic dialysis as described by Eichler et al., 1986, Clin. Pharmacol. Therap. 40: 300–303. Essentially, washed red blood cells were suspended in 1 ml of PBS (150 mM NaCl, 5 mM $K_2HPO_4$/$KH_2PO_4$; pH 7.4) to obtain a hematocrit of 60%. This suspension was placed in dialysis tubing (molecular weight cutoff 12–14,000; Spectra-Por) and swelling of cells was obtained by dialysis against 100 ml of 5 mM $K_2HPO_4$/$KH_2PO_4$, pH 7.4 for 90 minutes at 4° C. Resealing was achieved by subsequent dialysis for 15 minutes at 37° C. against 100 ml of PBS containing 10 mM glucose. Cells were then washed using centrifugation. In cases where electrosensitization was performed the method described in Example 1 was employed and cells were subsequently placed in PBS/Mg (Example 1) for 30 min at room temperature. All cells were subsequently stored in PBS/Mg/glucose (Example 1) prior to treatment with ultrasound.

Results 9

Figure 8:
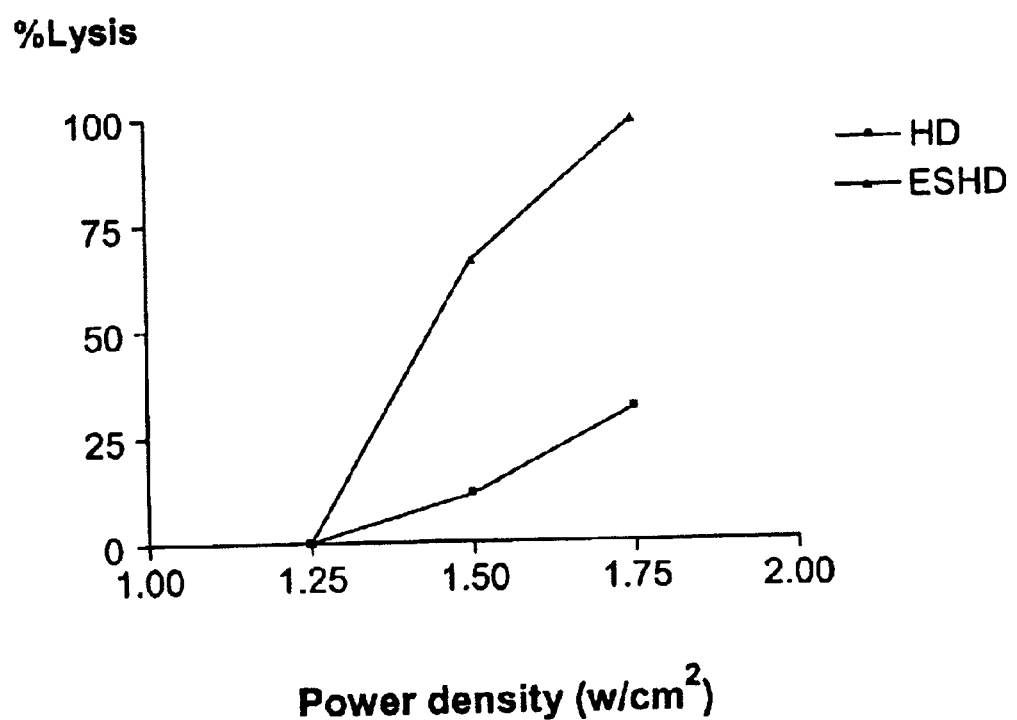
FIG. 8 shows the effects of ultrasound on (i) cells treated with hypotonic dialysis (HD) (■) and (ii) those treated with the hypotonic dialysis protocol, rested overnight at 4° C. and electrosensitized (▲). X-axis: power density (W/cm$^2$); Y-axis: % lysis.

Following hypotonic dialysis and exchange into PBS/Mg/glucose, cells were stored at room temperature for 1 hour. Both cells treated with hypotonic dialysis (HD) and electrosensitized cells which had been treated with hypotonic dialysis (ESHD) were then exposed to ultrasound at power densities of 1.25, 1.5 and 1.75 W/cm² and at a frequency of 3 MHz as described for Example 1. No significant lysis was observed in electrosensitized samples above that exhibited by control cells which were treated with hypotonic dialysis alone. Indeed at 1.25 W/cm² no lysis was observed in either sample and this contrasts significantly with results presented in FIG. 1, Example 1 where electrosensitized normal cells exhibited almost 100% lysis at that power density. When both the HD and ESHD cells were stored overnight at 4° C. and subsequently exposed to ultrasound, no significant lysis was detected. It was subsequently decided to electrosensitize the HD cells which had rested overnight. Following electrosensitization, cells were placed in PBS/Mg (Example 1) for 30 min. and subsequently placed in PBS/Mg/glucose for 1 hour. Cells (at a concentration of 5×10⁸ cells/ml were exposed to ultrasound at 1.25, 1.5 and 1.75 W/cm² as described above and the degree of lysis was determined. The results are shown in FIG. 8 and they demonstrate that the electrosensitized samples exhibited preferential lysis following exposure to ultrasound at 1.5 and 1.75 W/cm². The results from these experiments demonstrate that it is possible to render human red blood cells sensitive to ultrasound following treatment with alternative procedures designed to achieve loading of those cells. However, cell treated with the hypotonic dialysis method must be allowed to rest for a period of time prior to electrosensitization.

Example 10

Release of payload from loaded and sensitized vehicle in a tissue mimicking system (TMM).

Since the previous examples demonstrated that human erythrocytes could be sensitized to low intensity ultrasound, it was decided to show that a payload entity loaded into those sensitized erythrocytes could be released following exposure to low intensity ultrasound. In these experiments the target is placed at a distance of 1.3 cm from the emitting surface of the ultrasound head and the intervening space is filled with a tissue mimicking material (TMM) which attenuates ultrasound in the same manner as a soft tissue. The TMM chosen for this work is described in Madsen et al. (1998, Ultrasound Med. & Biol., 24, 535–542) and following preparation, care is taken to ensure that the material has a density of 1.03 g/ml.

In previous examples sensitized cells were employed as the target. In Example 9 above it is shown that cells which have been processed using technologies designed to load erythrocytes can be rendered sensitive by exposure to electric pulses. In order to demonstrate ultrasound-mediated payload release from the vehicle it was decided to employ a loaded vehicle as the target.

It was decided to employ a loading modality which incorporated a pre-sensitizing step prior to loading by hypotonic dialysis and subsequent exposure of those cells to an electrosensitizing step. The pre-sensitizing step is an optional step which increases the efficiency of a subsequent loading step, and is described in detail in our co-pending British Patent Application GB0002856.3. Thus, in this and the following examples in which RBCs are loaded with payload, a pre-sensitizing step is conducted to ensure optimal loading of payload into the RBCs. After loading of the agent, the cell is subjected to a second electrosensitizing step, which sensitizes the cell to ultrasound. As noted above, the pre-sensitizing step is optional, and identical or similar results are obtained when this step is omitted in the following examples.

Loading Protocol

This section describes protocols for the loading and sensitization of red blood cells by a combination of electrosensitization (ES) followed by hypoosmotic dialysis loading (HD). overnight rest and further treatment of the cells by electrosensitization. This combination is abbreviated as ES+HD+ES.

10 ml of peripheral venous blood is collected by venipuncture, into lithium heparin anticoagulant containing tubes and mixed gently. The whole blood is then poured into a polypropylene tube and centrifuged at 300 g for 15 min at room temperature. The plasma and white blood cells (buffy coat) are removed.

1×phosphate buffered saline (PBS, made from Oxoid tablets code BR14a pH7.3) is added and the cells centrifuged at 700g for 5 min. The supernatant is removed and the pellet of remaining cells resuspended in ice cold 1×PBS. The spin/wash procedure is then repeated once, and cells are suspended in ice-cold PBS at $6\times10^8$ cells/ml.

Cells are then electrosensitized by dispensing 800 ul of the RBC into sterile electroporation cuvettes, and placed on ice. To electrosensitize the cells, they are exposed to an electric field at 3.625 kV/cm, 1 uF (2 pulses), in the absence of payload. The RBCs are then removed, and pooled in polypropylene tubes.

Cells are centrifuged once at 700 g for 5 min at room temperature (RT). The cells may be diluted in PBS/$MgCl_2$ (4 mM). Cells are then resuspended in PBS/$MgCl_2$, and centrifuged at 700 g for 5 min, twice. Finally, cells are resuspended in PBS/$MgCl_2$, at approximately $7\times10^8$ c/ml, and rested for 30 min at room temperature.

Cells are then loaded with payload by hypo-osmotic dialysis, according to a protocol adapted from Eichler et al., (1986) Clin. Pharmacol. Ther. 40:300–303. Essentially the protocol is as follows:

1 REAGENTS AND BUFFERS:
Stock potassium phosphate buffer:
5 mm $K_2HPO_4$ $3H_2O$ (FW 228.2 g)⇒1.141 g/L
5 mM $KH_2PO_4$ (MW 136.1 g)⇒0.68 g/L
Stored at 4° C.
Mix as follows:
For a pH7.4 $K_2H$/$KH_2$ phosphate buffer⇒approx. 6.1:3.9 parts
Mix the 2 stock solutions as and when required
Buffer #1 (isoosmotic PBS):
pH7.4 $K_2H$/$KH_2$ phosphate buffer
150 mM NaCl⇒8.76 g/L
Check and adjust pH (1M NaOH)
Buffer #2 (dialysis buffer):
pH7.4 $K_2H$/$KH_2$ phosphate buffer
Check and adjust pH (1M NaOH)
Buffer #3 (resealing buffer)
pH7.4 $K_2H$/$KH_2$ phosphate buffer
150 mM NaCl⇒8.76 g/L
10 mM glucose⇒1.8 g/L
Check and adjust pH (1M NaOH)
SpectraPor DIALYSIS TUBING PREPARATION:
1 The 12–14 kDa MW cut off tubing, 0.32 ml/cm, is used.
2 Preparation: heat at 80° C./30 min in 1 mM EDTA/2% sodium bicarbonate (Sigma). Rinse well, inside and outside, with dd$H_2O$.
3 Wash inside and outside with Buffer #1
4 Store submerged in a small amount of Buffer #1 if not used immediately.
RBC PREPARATION:
1 Electrosensitized, rested RBC are washed in PBS twice at 700 g for 5 min.
2 For the final wash, cells are washed in buffer #1
3 The cells are manipulated as a suspension of packed cells following removal of final wash supernatants after centrifugation.
CELL VOLUME IN TUBING:
1 Protocol recommends 60% hematocrit (HCT). The suspension of packed cells is approximately 75% HCT and is diluted accordingly.
2 Mix cells with the payload and buffer #1, to give required final payload concentration and volume.
2 DIALYSIS:
1 The tubing is clipped to ensure that the surface area remains constant for the volume of cells.
2 Dialyze RBC (packed cell volume in buffer #1) against buffer #2 for 90 min at 4° C.
3 Place membranes in 100–200 ml buffer #2, (ensure that the membrane is immersed) in glass beaker with magnetic flea.
4 Place this beaker within another beaker, which contains ice, on the magnetic stirrer, cover with silver foil.
6 Warm up an aliquot of buffer #3 to 37° C.
7 Remove dialysis buffer, replace with the warm resealing buffer #3.
8 Place beaker with dialysis tubing and buffer #3 into a larger beaker anchored by water at 37° C., cover and leave for 15 min.
9 Harvest cells into 12 ml polypropylene tubes.
10 Wash×3 in ice cold resealing buffer #3 and spin at 300×g, 10 min 4° C.
11 Wash×1 in PBS/Mg/glucose and spin at 700×g, 5 min 4° C.
12 Count cells and resuspend at $7\times10^8$ c/ml, in PBS/Mg/glucose.
13 Store at 4° C. overnight.

In the present example, dialysis is performed in the presence of 1.5 mg of antibody per ml of cells. Cells are suspended at $7\times10^8$ cells/ml.

When cells have been loaded they are then sensitized by exposure to electric pulses as follows:

3 ELECTROSENSITIZATION
1 Following overnight storage, wash RBC once in PBS 700 g, 5 min 4° C.
2 Count cells and resuspend at $6\times10^8$ c/ml, in ice cold PBS.
3 Dispense 800 ul of the RBC into sterile electroporation cuvettes (0.4 cm gap).
4 Place on ice.
5 To electrosensitize: double pulse at 3.625 kV/cm, 1 uF.
6 Harvest the RBC, pool in a polypropylene tube.
7 Centrifuge once at 700 g for 5 min room temperature (RT). The cells may be diluted in PBS/$MgCl_2$(4 mM).
8 Resuspend in PBS/$MgCl_2$, centrifuge at 700 g for 5 min.
9 Repeat step 6
10 Resuspend in PBS/$MgCl_2$, at approximately $7\times10^8$ c/ml.
11 Rest the cells for 30 min at RT.
12 Centrifuge once at 700 g for 5 min room temperature (RT). The cells may be diluted in PBS/$MgCl_2$/glucose.
13 Resuspend the cells in PBS/$MgCl_2$/glucose, centrifuge at 700 g for 5 min.
14 Repeat step 13.
15 Resuspend cells in PBS/$MgCl_2$/glucose at $7\times10^8$ c/ml.
16 Rest the cells in PBS/$MgCl_2$/glucose for 60 min.

I. Ultrasound-mediated Release of Antibody from Vehicle

Antibody-loaded sensitized cells are then exposed to ultrasound at a distance of 1.3 cm from the emitting surface of the ultrasound head. The intervening space is filled with the TMM as described above and 0.1 ml aliquots of $7\times10^8$ cells/ml are exposed to ultrasound. In these studies a sheep anti-human von Willebrand factor antibody is employed as the payload in these studies. The amount of antibody in cells and released following treatment with ultrasound is quantified with an ELISA system, using standard protocols (as disclosed in for example, Harlow and Lane, Antibodies: a Laboratory Manual, (1988) Cold Spring Harbor, and Maniatis, T., Fritsch, E. F. and Sambrook, J. (1991), Molecular Cloning: A Laboratory Manual. Cold Spring Harbor, N.Y., Cold Spring Harbor Laboratory Press).

I. Results

Figure 9:
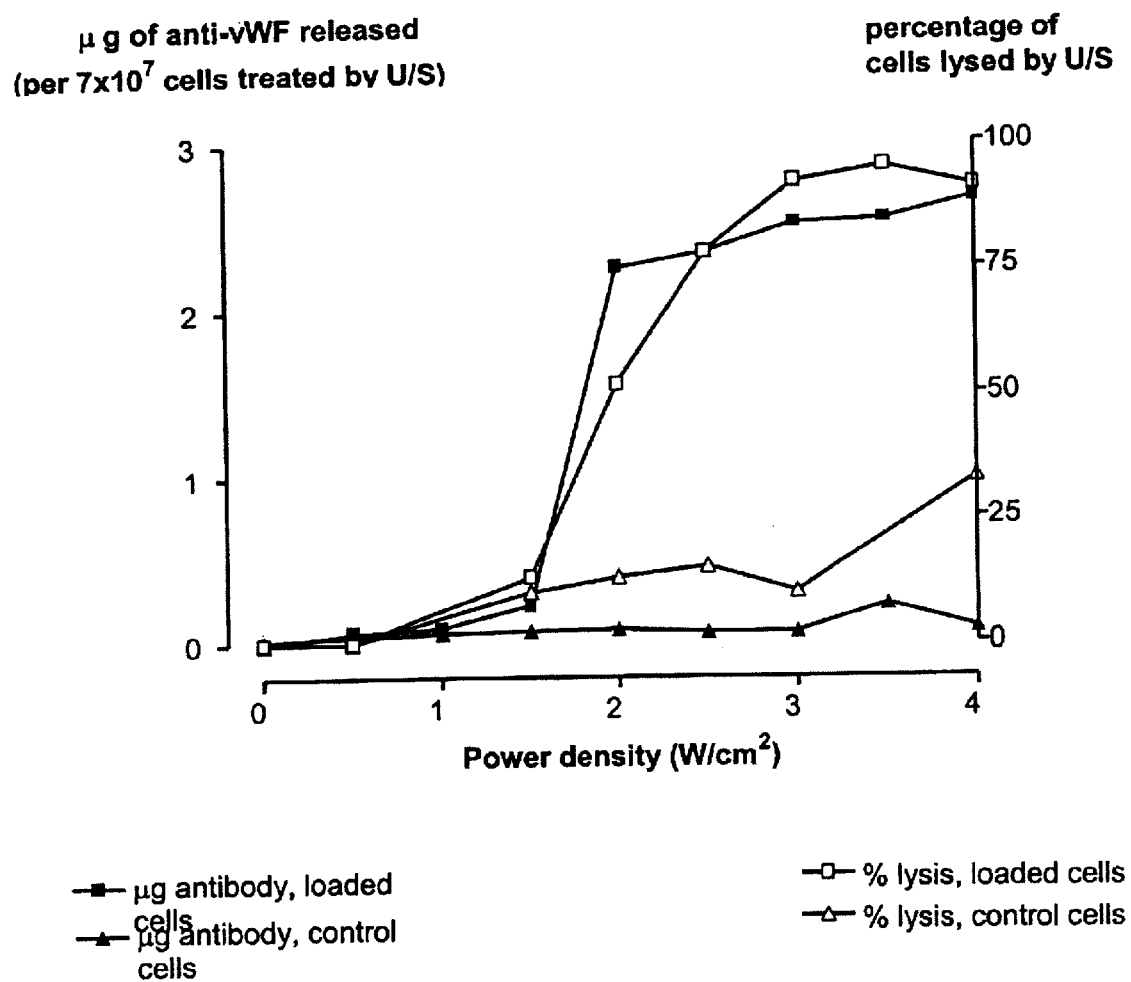
FIG. 9 is a graph showing the ultrasound-mediated release of antibody from the erythrocyte vehicle. X-axis: power density (W/cm$^2$), left hand Y-axis: μg of anti-vWF released (per 7×10$^7$ cells treated by ultrasound); right hand Y-axis: percentage of cells lysed by ultrasound. Filled squares represent μg antibody, loaded cells; filled triangles represent μg antibody, control cells; open squares represent % lysis, loaded cells; open triangles represent % lysis, control cells.

In the loading and sensitization protocol, cells are loaded at a concentration of 1.1 mg of antibody per ml of packed cell volume (PCV). 0.1 ml aliquots of cells at 7×10⁸ cells/ml are exposed to ultrasound at intensities shown in FIG. 9 and samples re analyzed for cell lysis by direct counting. In addition, the amount of antibody released following treatment with ultrasound is determined by ELISA analysis of cell supernatants harvested following centrifugation. The results obtained are shown in FIG. 9 and they demonstrate that cells were preferentially lysed at ultrasound power densities greater than 2 W/cm². Control cells exhibit little or no effect when treated with ultrasound at these power densities. At and above 2 W/cm² antibody payload is detected in supernatants harvested following ultrasound treatment. In addition, when the total amount of antibody released from the cells using ultrasound is compared with that released following hypotonic lysis in 0.01% (v/v) Triton X100 it is found that 77% of the total antibody is released in the former. The remainder could be found in debris that is recovered by centrifugation following ultrasound treatment.

The results demonstrate that ultrasound-mediated release of payload can be achieved using relatively low intensity ultrasound and using conditions which have little or no effect on normal erythrocytes. The results also demonstrate ultrasound-mediated release of payload at a depth of 1.3 cm and thereby demonstrating one of the major advantages associated with the use of ultrasound as the releasing stimulus of penetration to depth in tissues. Since all of the antibody incorporated into the ultrasound treatment experiments can be recovered as shown using an ELISA based on payload functionality, this suggests that the ultrasound has no detrimental effect on that functionality II. Ultrasound-mediated Release of Enzyme ((β-galactosidase) from Vehicle Cells are harvested, primed by exposure to electric pulses and loaded with β-galactosidase (from *Escherichia coli*, Sigma) as described above for antibody loading. Cells are subsequently exposed to sensitizing electric pulsing and exposed to ultrasound at a concentration of 7×10⁸ cells/ml in the TMM system as described above for the antibody-loaded vehicle. Lysates obtained following exposure of the loaded and sensitized vehicle to ultrasound are assayed for β-galactosidase activity at 37° C. using the colorimetric substrate p-nitrophenyl-β-D-galactoside (5 mM in 50 mM phosphate buffer, pH 7.0). The concentration of p-nitrophenol is determined spectrophotometrically at 450 nm and activity is expressed as μmoles of p-nitrophenol produced per minute per ml of sample. Release of enzyme in samples harvested following treatment with ultrasound is expressed as a percentage relative to the amount of enzyme contained in the cells prior to treatment. The latter is determined by measuring the amount of enzyme released from the cells following lysis by freeze-thaw in 5 mM phosphate buffer, pH 7.2.

II. Results

Figure 10:
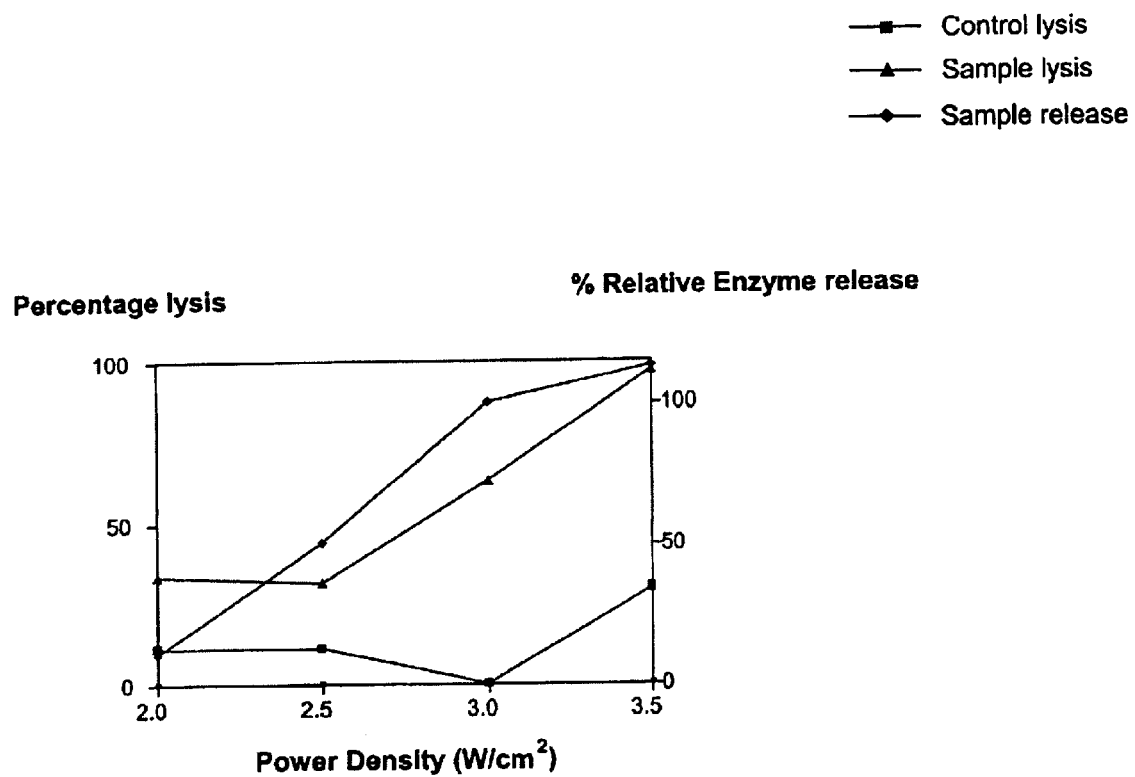
FIG. 10 is a graph showing ultrasound mediated release of β-galactosidase from the erythrocyte vehicle. X-axis: power density (W/cm$^2$), left hand Y-axis: percentage lysis; right hand Y-axis: % relative enzyme release. Filled squares represent control lysis, filled triangles represent sample lysis and filled diamonds represent sample release (i.e., release of enzyme).

In these experiments loaded cells contain approximately 1 mg of enzyme per ml of packed cell volume. The results obtained following treatment of these preparations with ultrasound are shown in FIG. 10. Samples are treated at the indicated power densities as shown and samples are analyzed for cell lysis by cell counting. Lysis increases with increasing power density up to a maximum at about 3 W/cm². Exposure of control normal cells to similar ultrasound conditions has little or no effect on cell lysis and this is confirmed by the absence of hemoglobin in supernatants following removal of cells by centrifugation. When supernatants are harvested by centrifugation, following exposure of the sensitized and loaded cells to ultrasound and analyzed for enzyme content, it is found that increasing amounts of enzyme are released with increasing power density up to a maximum at 3 W/cm².

The results demonstrate that enzyme is released from the vehicle following exposure to low intensity ultrasound. Ultrasound-mediated release of the payload is achieved at 1.3 cm from the emitting ultrasound head, indicating that the use of ultrasound for this purpose offers the advantage of penetration to depth in tissues. In addition, since 100% recovery of the enzyme released is achieved (between 2.5–3 W/cm²), the ultrasound stimulus resulting in release of enzyme has no detrimental effect on the functionality of the released payload.

III. Ultrasound-mediated Release of Oligonucleotide from Vehicle

Cells are harvested and primed by exposure to electric pulses as described above. Cells are then loaded using the hypoosmotic dialysis procedure described above for antibody loading and a 300 μg quantity of oligonucleotide (tamara labeled random 30-mer supplied by Oswel, UK) is mixed with 250 μl of packed cells. Samples are then subjected to electrosensitization electric pulses and subsequently suspended in PBS/MgCl₂/glucose at a concentration of 7×10⁸ cells/ml. Samples are exposed to ultrasound using the TMM system described above for antibody and enzyme release and the amount of oligonucleotide released is determined using a spectrofluorimeter (Shimadzu) with excitation set at 540 nm and emission set at 590 nm. A standard curve is constructed for quantitative determinations and extraction efficiencies are taken into account.

III. Results

Figure 11:
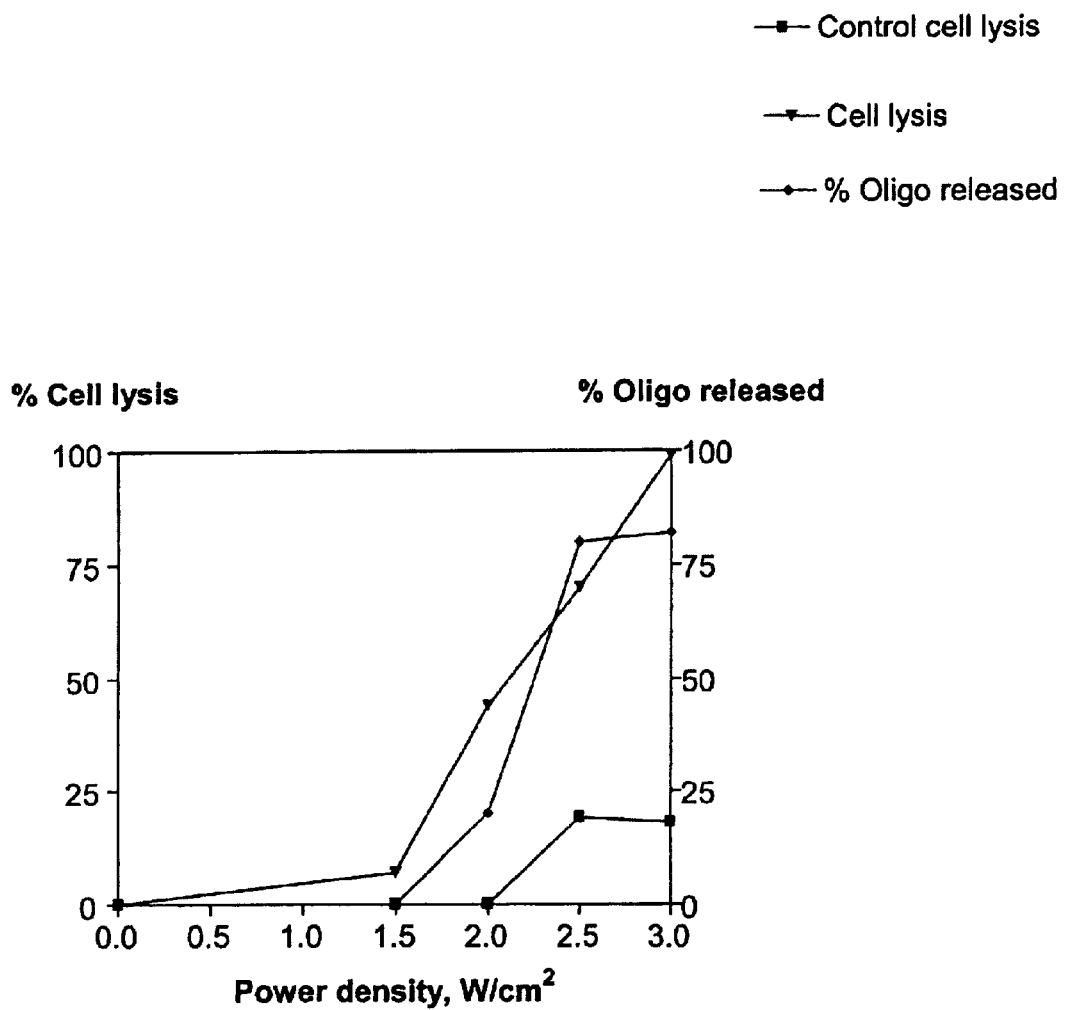
FIG. 11 is a graph showing ultrasound-mediated release of oligonucleotide from the erythrocyte vehicle. X-axis: power density (W/cm$^2$), left hand Y-axis: percentage cell lysis; right hand Y-axis: % oligo release. Filled squares represent control cell lysis, filled triangles represent cell lysis and filled diamonds represent % oligo released.

In these experiments the maximum amount of oligonucleotide loaded is approximately 300 kg of oligonucleotide per ml of packed cell volume. The results obtained following treatment of these loaded preparations with ultrasound are shown in FIG. 11. As with the above two examples, cell lysis of the sensitized and loaded preparation occurs between 2 and 3 W/cm². Under these ultrasound conditions there is little or no effect on control erythrocytes. In addition, oligonucleotide begins to appear in harvested supernatants between 2 and 3 W/cm² demonstrating ultrasound-mediated release of oligonucleotide payload from the vehicle. These results also demonstrate release of the payload from the vehicle when the target cells are at a distance of 1.3 cm from the emitting surface of the ultrasound head and this again indicates the advantage of penetration to depth in tissues associated with the use of ultrasound as a release stimulus.

Example 11

Ultrasound-mediated release of antibody payload in a perfused rat kidney system

Although it is demonstrated in the above examples that a variety of payloads can be released in a TMM system it is also of interest to demonstrate release of a functional payload in a tissue. To this end human erythrocytes are loaded with FITC-labeled anti-von Willebrand factor antibody and sensitized as described in Example 10 above. These cells are then administered to PBS-perfused rat kidneys and treatment with ultrasound is carried out according to the following protocol:

Perfuse the rat through the heart with PBS/EDTA until the kidney is clear of blood Remove the dorsal aorta from the heart and insert a gavage needle into the vessel. Tie the needle to the dorsal aorta using suture.

Close the dorsal aorta and posterior vena cava just after the junction leading to the kidney.

Close the left adrenal artery and vein and both anterior mesenteric and coeliac arteries Close the ureter and the left iliolumbar artery and vein.

Create an exit point by inserting a gavage needle into the vena cava just before the liver.

Tie needle using suture.

Flush with 10 ml PBS/4 mM Mg/10 mM glucose and check for any leakage.

Block the exit point by inserting 2 ml syringe into the gavage needle to establish positive pressure.

Load 1 ml of $7 \times 10^8$ cells/ml through the dorsal aorta into the kidney.

Treat with U/S using 1 MHz probe.

Incubate the treated kidney for one hour

Remove the 2 ml syringe and flush through with 2 ml PBS/Mg/glucose

Collect the flush through for cell counting and ELISA

Flush with 50 ml of PBS/EDTA

Flush with 20 ml of 4% neutral buffered formalin (NBF)

Remove the U/S-treated kidney and cut it into two half's and fix in NBF

Prepare tissue sections (12 um) and stain using Vectastain ABC kit (Vecta Labs) as outlined in the manufacturer's instructions.

Results 11

Figure 12:
FIG. 12 shows ultrasound-mediated release of anti von Willebrand factor antibody from sensitized human erythrocytes in perfused rat kidney.
Figure 12:
Figure 13A:
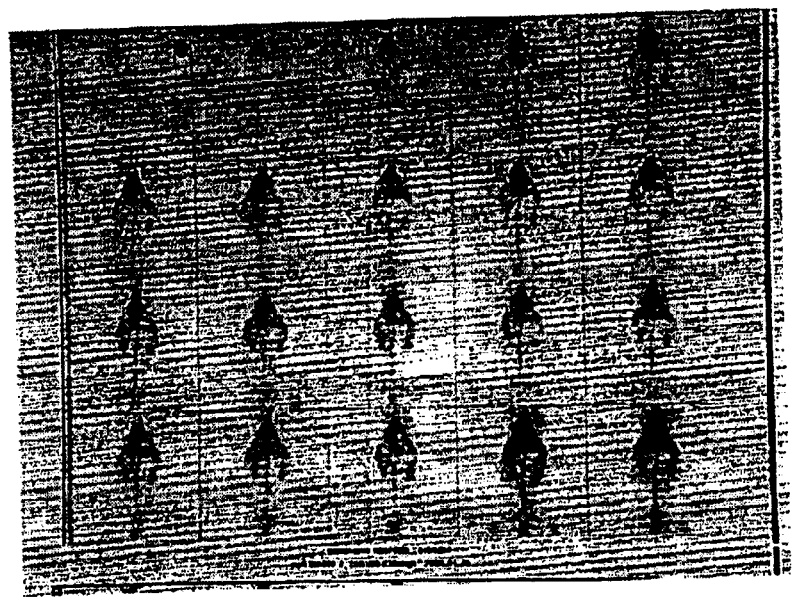
FIGS. 13A, B and C: first row 10", 30", 1', 1'30", 2'; second row 2'30", 3', 4', 5', 6'; third row 7', 8', 9'30", 11', 12'30"; fourth row 14', 15'30", 16', 18'30", 20'.
Figure 13B:
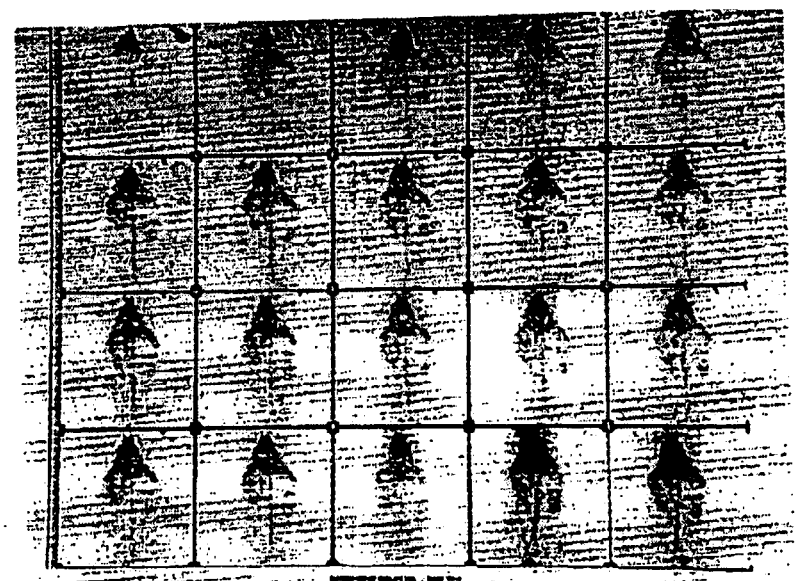
FIG. 13 shows gamma camera imaging of $^{99}$Tc labeled electrosensitized (A), normal (B), glutaraldehyde-treated (C) and PEGylated (D) rabbit erythrocytes during circulation in a host rabbit. Images were captured over a 20 min. period at intervals.
FIG. 13D: row 1 10s, 20s, 30s, 40s, 50s, 1', 70s, 80s; row 2 90s, 100s, 110s, 2', 130s, 140s, 150s, 160s; row 3 170s, 3', 3'20s, 3'40s, 4', 4'20s, 4'40s, 5'; row 4 5'20s, 5'40s, 6', 6'20s, 6'40s, 7', 7'20s, 7'40s; row 5'8, 8.5', 9', 9.5', 10', 10.5', 11', 11.5'; row 6 12', 12.5', 13', 13.5', 14', 14.5', 15', 15.5'; row 7 16', 16.5', 17', 17.5', 18', 18.5', 19', 19.5'.
Figure 13C:
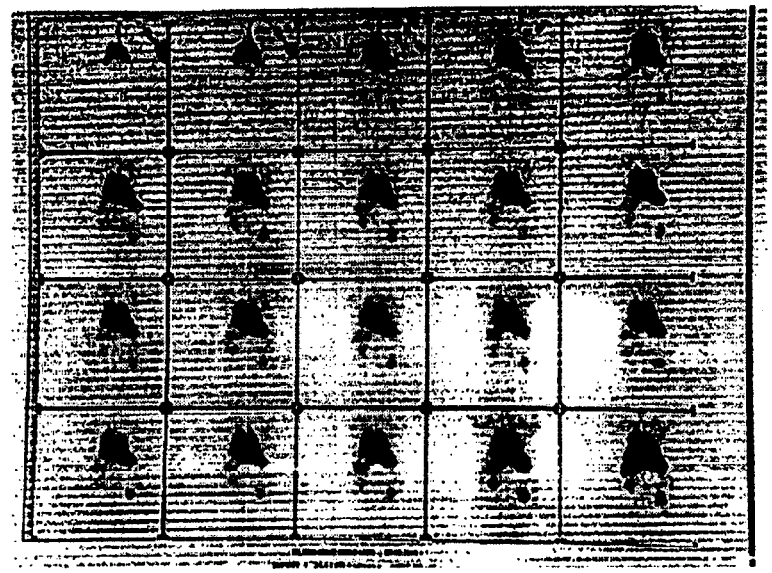
Figure 13D:

As shown in FIG. 12, kidney endothelial cells in glomeruli are labeled with the FITC conjugated anti-vWF antibody after ultrasound treatment to release the antibody (+U/S). In the absence of ultrasound treatment, no staining is observed ([-U/S]). The results demonstrate that low intensity ultrasound may be used to effect release of functional antibody from the loaded and sensitized vehicle in a perfused tissue system.

Example 12

Circulation of normal, electrosensitized, glutaraldehyde-treated and PEGylated normal rabbit erythrocytes in vivo.

Since it is widely known that damaged erythrocytes are rapidly removed from circulation by macrophages of the reticulo-endothelial system (DeLoach and Barton, 1981, *Am. J. Vet. Res.* 42, 1971–1974), it is of interest to determine whether or not electrosensitized erythrocytes remain in circulation. As mentioned above it has also been demonstrated that PEGylation has the ability to protect foreign entities from recognition by reticulo-endothelial system and to this end it was decided to PEGylate normal erythrocytes and demonstrate that the modification prevented recognition by that system. In order to examine the above, it was decided to examine circulation of normal, electrosensitized, PEGylated and glutaraldehyde-treated rabbit erythrocytes in vivo. The latter treatment is chosen as a positive control for sequestration by the reticulo-endothelial system since it has been shown to promote targeting by the RES and consequential rapid uptake by the liver/spleen. In these studies circulation of the labeled vehicle is monitored by firstly labeling the cells with $^{99}$Tc and subsequently monitoring the fate of that label using a gamma camera and acquiring full body scans of the recipient animal.

To the above ends peripheral rabbit venous blood is obtained by venipuncture, and added to tubes containing lithium heparin anti-coagulant. The donor rabbits are male and female New Zealand white rabbits which weighed between 3 kg and 4 kg. Whole blood is centrifuged at 300 g for 15 minutes at room temperature. Plasma and white cells are removed and the cell pellet resuspended to 10 ml in cold PBS. Cells are washed twice at 800×g for 3 minutes and the pellets resuspended with cold PBS. Erythrocytes are diluted in PBS and counted as described above. Peripheral venous blood collected as described previously is aliquoted into Eppendorf tubes and centrifuged at 800 g for 3 minutes at room temperature. Plasma is harvested and stored in Eppendorf tubes at room temperature until required.

In cases where cells are electrosensitized, RBC are resuspended at between $7–8 \times 10^8$ cells/ml in cold PBS. Seven hundred µl of the cell suspension and 100 µl of cold PBS are added to sterile electroporation cuvettes. Cuvettes are mixed and pulsed twice at 1.45 kV and 1 µF with a BioRad electroporator. Cells are harvested into Eppendorf tubes, centrifuged once then washed twice with 1 ml of cold PBS at 800×g for 3 minutes. The final pellet is resuspended with 760 µl of cold PBS/4 mM MgCl$_2$. Cells are left on ice for 30 minutes. Next the cells are washed in a buffer (145 mM NaCl, 2.4 mM KCl, 7.6 mM Na$_2$HPO$_4$2H$_2$O, 2.4 mM NaH$_2$PO$_4$2H$_2$O, 4 mM MgCl$_2$, 10 mM glucose). Ultrasound sensitivity following electrosensitization is verified by exposing the cells to 3 W/cm$^2$ for 35 sec. on the TMM system and using the 1 MHz ultrasound head.

In cases where cells are PEGylated the procedure is that described in Scott et al PNAS 94:7566 1997. Cells are washed at 800×g for 3 minutes, resuspended in cold PBS, pooled and counted. Counts are typically between $7–8 \times 10^8$ cells/ml. In order to determine whether PEGylation is successful 1 µl of the appropriate agglutinating IgM antibody (Lorne Laboratories Ltd) is added to 10 µl of a 1:2 dilution of PEGylated RBC and to 10 µl of a 1:2 dilution of non-PEGylated RBC. The glass slides are rocked gently, agglutination is observed in non-PEGylated samples but not in the PEGylated samples.

Cells are glutaraldehyde treated as follows: 1 ml of packed cells are technetium labeled as described above. 0.5 ml of glutaraldehyde at 2.5% v/v was then added to the labeled cells, and the preparation allowed to stand for 5 minutes at room temperature. Cells are then washed twice with PBS.

In all cases, preparations of cells are $^{99}$Tc labeled for monitoring purposes in vivo. Essentially one ml of the prepared RBC (between $7–8 \times 10^8$ c/ml) and 0.5 ml of autologous plasma are mixed and then injected into the technetium kit as per the kit protocol (Mallinckrodt UK Ltd, Bichester, UK). Following labeling, the contents of the kit are harvested and the cells washed 3 times in PBS at 800×g for 3 minutes. Supernatants are retained to check the levels of radioactivity. The final cell pellets are resuspended in 1 ml of PBS and the cells counted. The cells are then injected into the right ear of the rabbits (male or female New Zealand white rabbits, which weighed between 3 and 4 kg). Following injection, the fate of circulating RBC is monitored with a gamma camera and whole body images are acquired at times ranging from time zero to 20 minutes.

Results 12

Results are presented as four panels in FIGS. 13 A, B, C, and D representing whole body scans of rabbits injected with electrosensitized, normal, glutaraldehyde treated normal and PEGylated normal rabbit erythrocytes, respectively. In panels A to C, whole body scans are captured at the times indicated in FIG. 13 over a period of time zero to 20 minutes. In FIG. 13, panel B the distribution of labeled normal erythrocytes is seen over this time period and represents a normal distribution. Liver, kidneys and ventral line vasculature to fermorals are clearly imaged and no preferential accumulation in the liver-spleen is seen in the images. The distribution of electrosensitized rabbit cells (FIG. 13, Panel A) over the scanning time period is similar to that exhibited by normal cells and from this one can conclude that the half life of the sensitized cells mimics that of normal cells. No preferential accumulation in the liver or spleen over that exhibited by the normal cells is apparent. As mentioned above, glutaraldehyde treatment of erythroyctes promotes recognition by the reticulo-endothelial system with the consequence of rapid sequestration by the liver and spleen. FIG. 13, panel C clearly shows dramatic premature accumulation of the radioactively labeled glutaraldehyde-treated cells in the liver and spleen of the recipient rabbit. On the basis of comparison between the distribution of normal, electrosensitized and glutaraldehyde-treated normal cells over the scanning time period it is clear that the circulation of electrosensitized cells is not compromised by any modification resulting from the electrosensitization procedure. The results suggest that the use of electrosensitized erythrocytes as a vehicle for payloads offers the advantage over competing technologies (e.g. liposome technology) in that they are not recognized by the reticulo-endothelial system, thereby offering prolonged circulation times in vivo.

In addition, when PEGylated normal erythrocytes are introduced into a recipient animal, it is found that their distribution during circulation over the scanning time examined is normal (FIG. 13, Panel D). In this case scan capture is more frequent as indicated, but the overall scan time again ranged from time zero to 20 minutes. This latter result suggests that PEGylation of erythrocytes does not cause damage which results in recognition of the modified cells by the reticulo-endothelial system and further suggests that if our carrier erythrocyte technology requires PEGylation for what ever reason, then it may be applied without negative consequence in terms of premature removal from circulation.

Example 13

The effect of PEGylation on circulation of human erythroyctes in the rabbit

As mentioned above PEGylation of foreign entities aids in preventing recognition by macrophages of the reticulo-endothelial system. In order to determine whether or not PEGylation facilitates prolonged circulation of species-heterologous erythroyctes it was decided to examine circulation of normal, PEGylated normal and PEGylated electrosensitized human erythroyctes in rabbits using the $^{99}$Tc-based monitoring method described above.

To this end, peripheral venous blood is obtained by venipuncture, and added to 10 ml blood collection tubes containing lithium heparin anti-coagulant. Donor phenotype is determined by agglutination with antisera from Lorne Laboratories Ltd, (Twyford, UK). Aliquots (1 ml) of whole blood was added to Eppendorf tubes and centrifuged at 300 g in a centrifuge (Heraeus Biofuge pico), for 15 minutes at room temperature. Plasma and white cells are removed and the cell pellet is resuspended to 1 ml in cold (4° C.) phosphate buffered saline (PBS, Oxoid, Basingstoke, UK). Cells are washed at twice at 800 g for 3 minutes, in cold PBS. Pellets are resuspended to a final volume of 12 ml with cold PBS. Erythrocytes/red blood cells (RBC) are diluted 1 in 200 and counted with a hemocytometer. Peripheral venous blood collected as described previously is aliquoted in Eppendorf tubes and centrifuged at 800×g for 3 minutes at room temperature. Plasma is harvested and stored in Eppendorf tubes at room temperature until required. In cases where electrosensitization and PEGylation are required, these were performed as described above for Example 12.

One ml of the prepared RBC (between 7–8×10$^8$ c/ml) and 0.5 ml of autologous plasma are mixed and then injected into the technetium kit as per the kit protocol (Mallinckrodt UK Ltd, Bichester, UK). Following labeling, the contents of the kit are harvested and the cells washed 3 times in PBS at 800×g for 3 minutes. Supernatants are retained to check the levels of radioactivity. The final cell pellets re resuspended in 1 ml of PBS (with the exception of (+) EP cells which are resuspended in 0.5 ml of PBS) and the cells counted. The cells are then injected into the right ear of the rabbits (male or female New Zealand white rabbits, which weighed between 3 and 4 kg). Following injection, the fate of circulating RBC is monitored with a gamma camera. The accumulated images are analyzed by specialized computer packages. The circulation time of RBC is analyzed by monitoring circulating labeled erythroyctes in the heart.

Results 13

Figure 14:
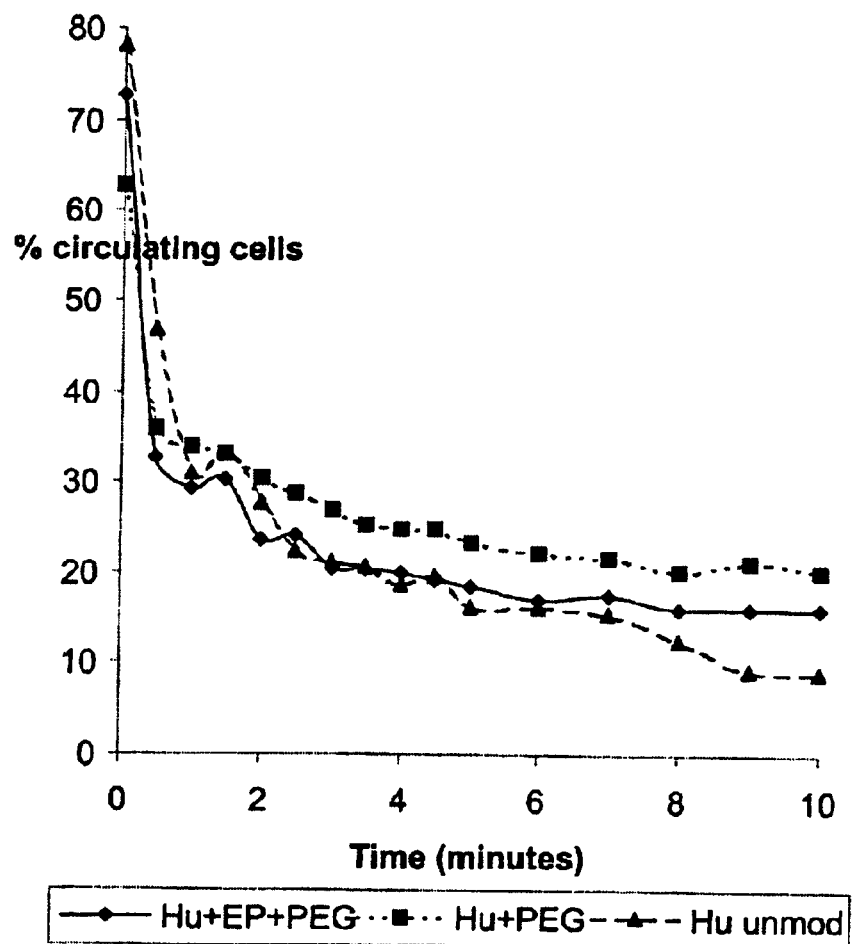
FIG. 14 shows clearance of $^{99}$Tc-labeled normal (▲), PEGylated normal (■) and PEGylated electrosensitized (♦) human erythrocytes during circulation in a recipient rabbit. X-axis: Time (minutes), Y-axis: %circulating cells.

The results obtained from these experiments are shown in FIG. 14. When labeled normal, PEGylated normal and PEGylated electrosensitized cells are introduced into recipient rabbits, the proportion of labeled cells remaining in circulation drops to approximately 35% within 1 minute. However, at time intervals following that stage, the advantage associated with PEGylation becomes apparent particularly at 10 minutes. At 10 minutes the unmodified normal human cells continue to decrease in circulation whereas survival of the PEGylated normal and PEGylated human cells in circulation is enhanced.

The results suggest that if species-heterologous or modified autologous/homologous sensitized erythroyctes are to be employed as a delivery vehicle, recognition by the macrophages of the reticulo-endothelial system and consequential removal from circulation can, at least in part, be prevented by PEGylation.

Example 14

Since the above studies demonstrate that sensitized rabbit erythroyctes are stable during circulation in vivo it was decided to confirm these results using an alternative labeling method and monitoring system. It has been shown that erythrocytes may be conveniently labeled using the fluorogenic label PKH-26 which incorporates into the membrane of the cell (Selzak & Horan, 1989, Blood, 74, 2172–2172). Cells may therefore be introduced into a recipient animal and monitored using flow cytometry. If this system can be employed to monitor normal (autologous, heterologous rabbit) and electrosensitized rabbit cells during circulation in vivo it will circumvent problems associated with the relatively short half life of $^{99}$Tc.

Cells are harvested and where required, electrosensitized as described above in Example 12. Cells are then PKH-26 labeled as follows:

1—Remove 5 ml of blood from rabbit ear vein
2—Wash twice to remove buffy coat in saline and process cells as required for treatment
3—Re-suspend cells in saline to give a packed cell volume of ~0.25 ml
4—Centrifuge & remove supernatant
5—Add 1 ml of PKH-26 labeling kit buffer C (Sigma #MINI-26) & resuspend cells
6—To 1 ml of buffer C add 4 µl of 1 mM PKH-26 solution, mix well & add to cell suspension 7—Mix tube by gentle inversion for 5 minutes
8—Spin for 10'
9—Remove supernatant & wash 3 times in saline
10—Count cells & resuspend in 1 ml of saline
11—Verify cell labeling using flow cytometry Following labeling cell preparations (0.5 ml packed cells) are injected into the rabbit ear vein (recipient animal weighs between 3 and 4 kg). At the indicated times 50 µl samples are collected into 1 ml of heparin-containing saline. Samples are subsequently analyzed using flow cytometry and the percentage of labeled cells in circulation is determined.

Results 14

Figure 15:
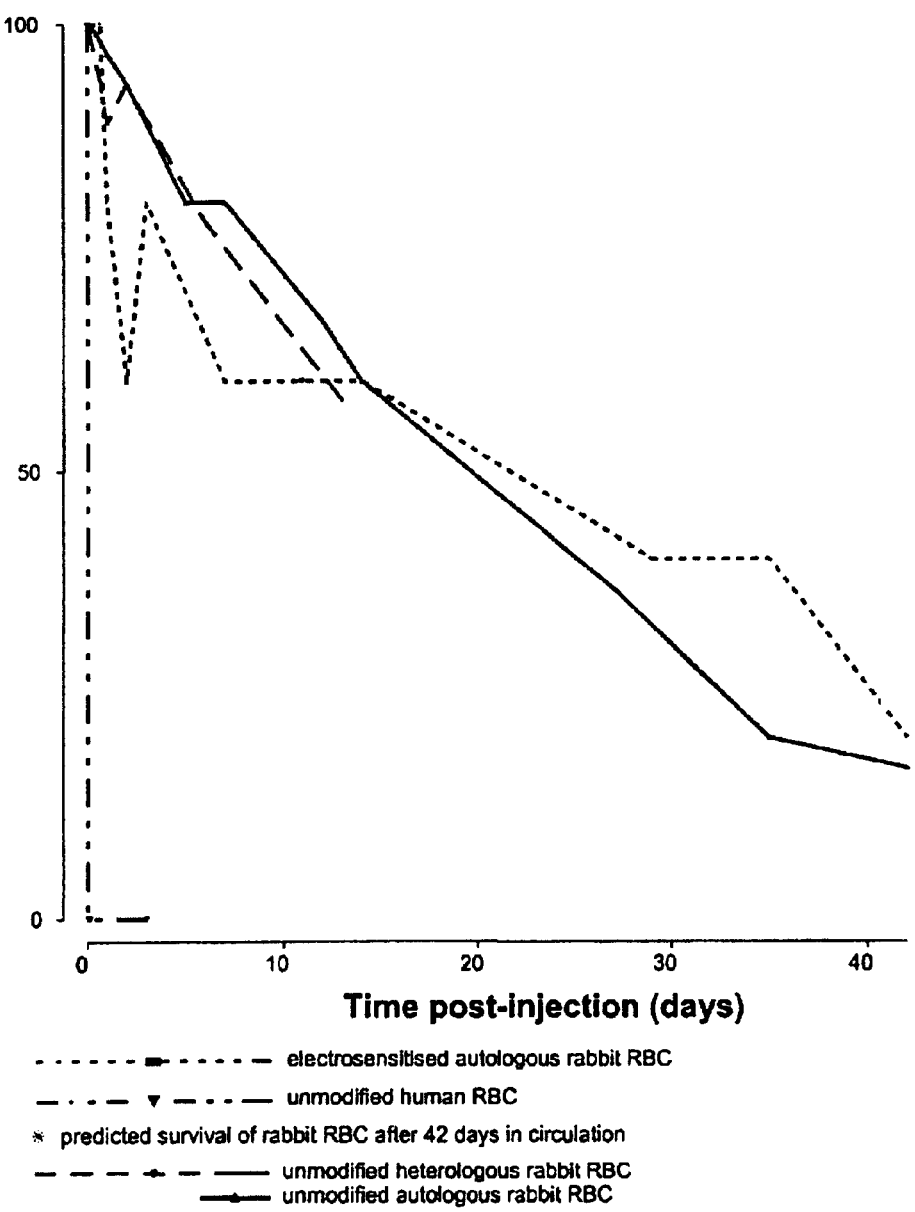
FIG. 15 shows in vivo survival of PKH-26 labeled, normal autologous, normal heterologous and electrosensitized rabbit erythrocytes in recipient rabbits. X-axis: time post-injection (days); Y-axis % of PKH-26 labeled cells remaining in circulation. Normal human erythrocytes are included as a control for sequestration by the reticuloendothelial system, — (continuous) unmodified autologous rabbit RBC; ——— unmodified heterologous rabbit RBC; - -- electrosensitized autologous rabbit RBC; —- —-- Unmodified human RBC; * predicted survival of rabbit RBC after 42 days in circulation.

Rabbits are injected with PKH-26 labeled rabbit normal autologous, normal heterologous and electrosensitized cells. PKH-26 labeled human erythrocytes are used as a control for reticulo-endothelial scavenging. Samples are harvested at the indicated times and the labeled cells in circulation expressed as a percentage of the amount detected at time zero are detected by flow cytometry. The results obtained are shown in FIG. 15 and they demonstrate that PKH-26 labeled normal autologous and heterologous rabbit cells circulate normally (see FIG. 15 for predicted status of normal cells based on published $T_{1/2}$ for normal rabbit erythrocytes [from Vomel & Platt, 1981, Mech. Aging Dev. 17, 261–266]). In addition, PKH-26 labeled electrosensitized cells are also shown to circulate with pharmacokinetics similar to those exhibited by normal cells (FIG. 15). On the other hand human cells are rapidly cleared from circulation. The results confirm our earlier findings that electrosensitized cells circulate with pharmacokinetics similar to those exhibited by normal circulating rabbit cells.

Example 15

Survival of loaded and electrosensitized erythroyctes in vivo

As shown above, electrosensitized cells are stable during circulation in vivo. It is also of interest to determine whether or not cells which are electrosensitive and also processed through a loading protocol such as hypotonic dialysis loading, remain intact during circulation. It was therefore decided to produce ultrasound sensitive erythroyctes loaded with antibody (rabbit anti-human IgG) and introduce them into an animal. The cells are PKH labeled and their circulation in vivo is monitored using flow cytometry as described above.

Rabbit erythrocytes are harvested and washed by centrifugation in PBS. Erythroyctes are loaded and sensitized by a modification of the procedure devised for human cells and described in detail as follows:

Buffers and Solutions

PBS: Phosphate buffered saline tablets (Oxoid: Code BR14a) made up as per instructions PBS-Glutathione: Above supplemented with 0.5 mM reduced glutathione PBS-MgCl$_2$-Glutathione: PBS (above) supplemented with 4 mM MgCl$_2$ and 0.5 mM reduced glutathione.

Dialysis buffer (hytonic): 12.5 mM K$_2$HPO$_4$/KH$_2$PO$_4$ containing 0.5 mM reduced glutathione, pH 7.4

PIGPA: 5 mM adenine, 100 mM inosine, 2 mM ATP, 100 mM sodium pyruvate, 100 mM glucose, 4 mM MgCl$_2$, 194 mM NaCl, 1.6 mM KCl, 35 MM NaH$_2$PO$_4$, pH 7.4

BAX/0.5 mM Glutathione: PBS (as above) supplemented with 5 mM adenosine, 5 mM glucose, 5 mM MgCl$_2$ and 0.5 mM reduced glutathione, pH 7.4.

Dialysis Tubing Preparation

Dialysis Tubing: Spectra/Por® Membrane MWCO: 12–14,000 No. 2

Flat Width: 10+/−1 mm
Diameter: 6.4 mm

Method:

Day one
1—Collect 10 ml of blood from rabbit ear vein into 10 ml heparinized tube
2—Transfer blood to 15 ml tube & spin at 3,000 rpm for 3' at RT°
3—Remove plasma & buffy coat
4—Add equal volume of PBS, re-suspend & spin at 2,000 rpm for 15' RT°
5—Repeat step4
6—Aliquot 0.5 ml of packed cells plus 1 mg of Rb α-Hu IgG into the dialysis tubing.
7—Place tubing into a 3 ml electroporation cuvette & fill the cuvette with PBS-GSH.
8—Electroporate at RT°, 5 kV/cm, 3 µF, double pulse.
9—Remove dialysis tubing immediately & place into 100 ml of dialysis buffer on ice. Dialyze with stirring for 30'.
10—Transfer tubing to tubes containing 30 ml of PBS-MgCl$_2$ & incubate for 11' at 37° C. with intermittent agitation of tubes.
11—Transfer the contents to 1.5 ml Eppendorf tube & measure the volume. Add PIGPA to the tube at $\frac{1}{10}^{th}$ the volume & incubate at 37° C. for 30'.
12—Transfer to a 15 ml tube & bring the volume to 2 ml with Bax buffer at RT.
13—Centrifuge cells at 900 rpm for 5'.
14—Resuspend cells in 2 ml Bax buffer & store O/N at 4° C.

Day two
1—Following O/N storage centrifuge samples at 900 rpm for 5' at 4° C.
2—Remove supernatant and resuspend to 4 ml with Bax buffer & wash twice at 900 rpm for 5', followed by 1×1400 rpm centrifugation for 5'
3—Resuspend samples initially in 2 ml of Bax buffer & pool samples into a 15 ml tube on ice & remove a small sample. Adjust volume of the sample to give a cell concentration of 7×10$^8$ cells/ml
4—Verify ultrasound sensitivity (1 MHz, 1.25 W/cm$^2$, 15 seconds)

The loaded and sensitized cells are then labeled with PKH-26 as described above and again ultrasound sensitivity is verified. In these experiments 1×10$^9$ cells are injected into a rabbit (3 kg) which is anaesthetized by injection with a 0.3 ml Vetalar/0.2 ml Rompun mixture into the left ear vein. A 50 µl sample is taken prior to injection and placed in 450 µl of PBS containing heparin. Subsequent samples are taken at the times indicated in a similar manner post injection of labeled cells and samples are analyzed by flow cytometry.

Results 15

Figure 16:
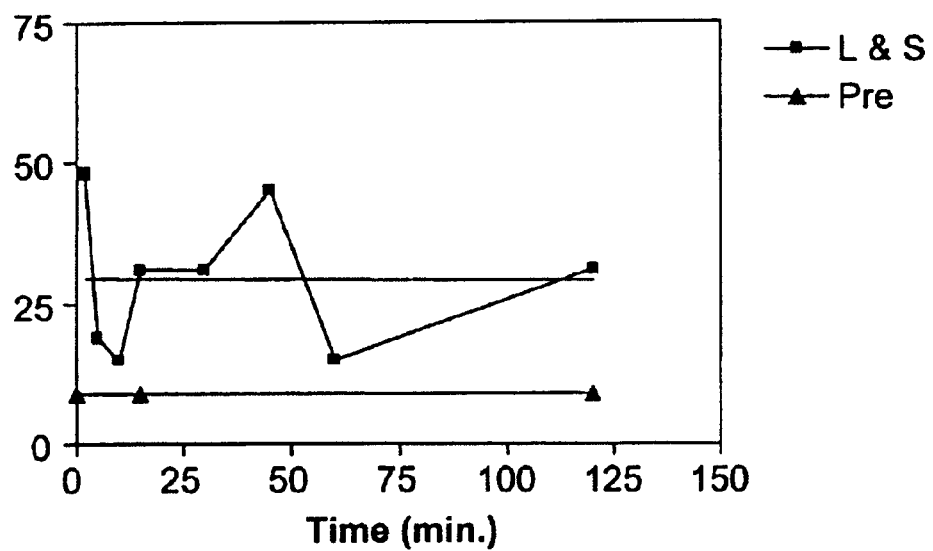
FIG. 16 shows survival of PKH-26-labeled antibody-loaded and sensitized rabbit erythrocytes in vivo. X-axis: time (min); Y-axis: counts of labeled cells. The base line indicated by ▲ is for reference purposes and indicates the level of counts detectable prior to introduction of the labeled erythrocytes. Filled squares represent loaded and sensitized rabbit erythrocytes.

The results obtained are shown in FIG. 16 and they demonstrate that counts of labeled cells remain above background throughout the period examined. The line indicated by upright triangles is simply for reference to the counts detected in the blood sample taken prior to injection of the labeled cells. The results demonstrate that approximately 70% of the introduced cells remain at two hours. It should be noted that if these cells are being recognized by the reticulo-endothelial system, clearance should occur within 5 minutes. Since this does not occur the results clearly demonstrate that the loaded and sensitized vehicle is relatively stable during circulation in vivo.

Example 16

Ultrasound-mediated release of payload from the loaded, sensitized vehicle in a circulating system at 37° C. and at high hematocrit (Hct.)

In the above studies it is shown that human erythroyctes can be sensitized to low intensity ultrasound and ultrasound-mediated disruption and/or payload release can be achieved in vitro and in an ex vivo perfused rat kidney system. In all of those systems disruption and/or payload release is demonstrated at $7 \times 10^8$ cells/ml which is approximately equivalent to a 5% Hct. In addition, those studies are performed at room temperature. Since Example 12 demonstrates that human cells are rapidly cleared from circulation in an animal model system it is of interest to demonstrate that sensitivity in terms of payload release can be retained at 37° C. and at higher Hct. It is also of interest to determine whether or not this occurs while the target cells are moving through a circulation system in much the same as those circulating in vivo.

To these ends human erythrocytes are harvested and loaded with anti-von Willebrand factor antibody as described for Example 10. Following sensitization cells re mixed together with normal washed human cells in the proportions of one part $7 \times 10^8$ cells/ml and four parts $4 \times 10^9$ cells/ml. The mixture is introduced into a circulating system consisting of a cylindrical reservoir filled with PBS and maintained at 37° C. by circulation. The bottom of the cylinder consists of a light polyethylene sheet through which ultrasound is delivered. The blood is circulated through C-flex tubing (internal diameter 4 mm) which passes through the thermostated buffer and the target area of the C-flex tubing is positioned at a distance of 1.3 cm from the ultrasound-emitting head. Blood is circulated through the system at a rate of 14.5 ml/min. During exposure to ultrasound (5 W/cm$^2$ at 1 MHz for indicated times), samples are harvested from the system and supernatants are harvested by centrifugation. These are then assayed for antibody using an ELISA assay as described above. The control in these experiments consists of loaded and sensitized cells circulated through the system in the absence of ultrasound. It is also important to note that circulation of normal cells through the system while ultrasound is being delivered results in no apparent damage as determined by the lack of hemoglobin in supernatants following treatment.

Results 16

Figure 17:
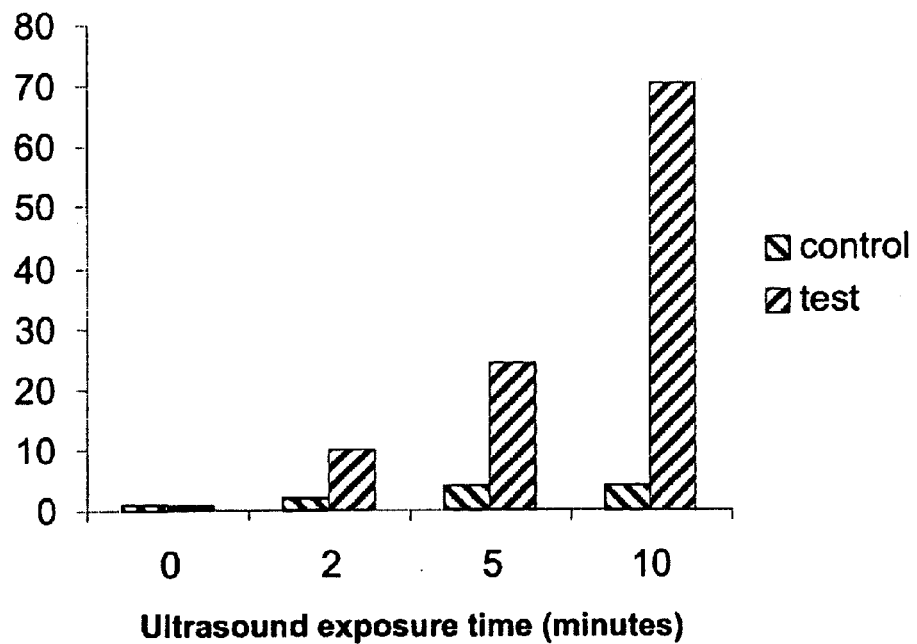
FIG. 17 shows ultrasound-mediated release of antibody payload (anti-von Willebrand factor antibody) from loaded and sensitized human cells diluted in normal human cells at 40% hematocrit. Continuous wave ultrasound at 5 W/cm$^2$ is used. X-axis: ultrasound exposure time (minutes); Y-axis: antibody payload released (%). The target cells were circulated through a system in which the temperature was maintained at 37° C. and the flow rate during exposure was 14.5 ml/min. Gray bars: control; black bars: test.

The results are shown in FIG. 17 and they demonstrate that detectable quantities of antibody are released from the vehicle between 2 and 5 minutes treatment with ultrasound. Little or no antibody can be detected in control samples which consist of the loaded and sensitized cells circulated through the system in the absence of ultrasound. The results demonstrate that the ultrasound-sensitization phenomenon is intact at 37° C. and ultrasound-mediated release of payload is achieved at high hematocrit (Hct.) and in a mobile target system.

Example 17

Circulation of Payload and Detection Limits

Since it has been demonstrated in the above examples that loaded and sensitized rabbit erythrocytes are relatively stable in vitro it was decided to examine ultrasound-mediated release of payload in the rabbit. In these studies rabbit anti human IgG is chosen as the payload and quantified using an ELISA system based on recognition of human IgG. Prior to embarking on in vivo studies involving release of antibody from the vehicle, it was decided to examine circulation of the payload alone in order to demonstrate that it is not prematurely removed from circulation. This was also carried out in order to determine the detection limits of the antibody in plasma during circulation.

To this end rabbits (approx. 3 kg) are anaesthetized by injection with 0.3 ml Vetlar and 0.2 ml Rompun into the ear vein. Antibody is injected into the recipient rabbits at a concentration of 0.5 mg/kg. A 50 µl sample of blood is harvested prior to injection of antibody and mixed together with 450 µl of PBC containing heparin. Following administration of antibody 50 µl samples are harvested at the indicated times and mixed together with 450 µl of PBS containing heparin. Samples are then centrifuged at 2000 rpm using a microfuge and the supernatants are aliquoted into 150 µl quantities for storage at −80° C. Samples are analyzed for antibody content using an ELISA method based on recognition of human IgG.

Results 17

Figure 18:
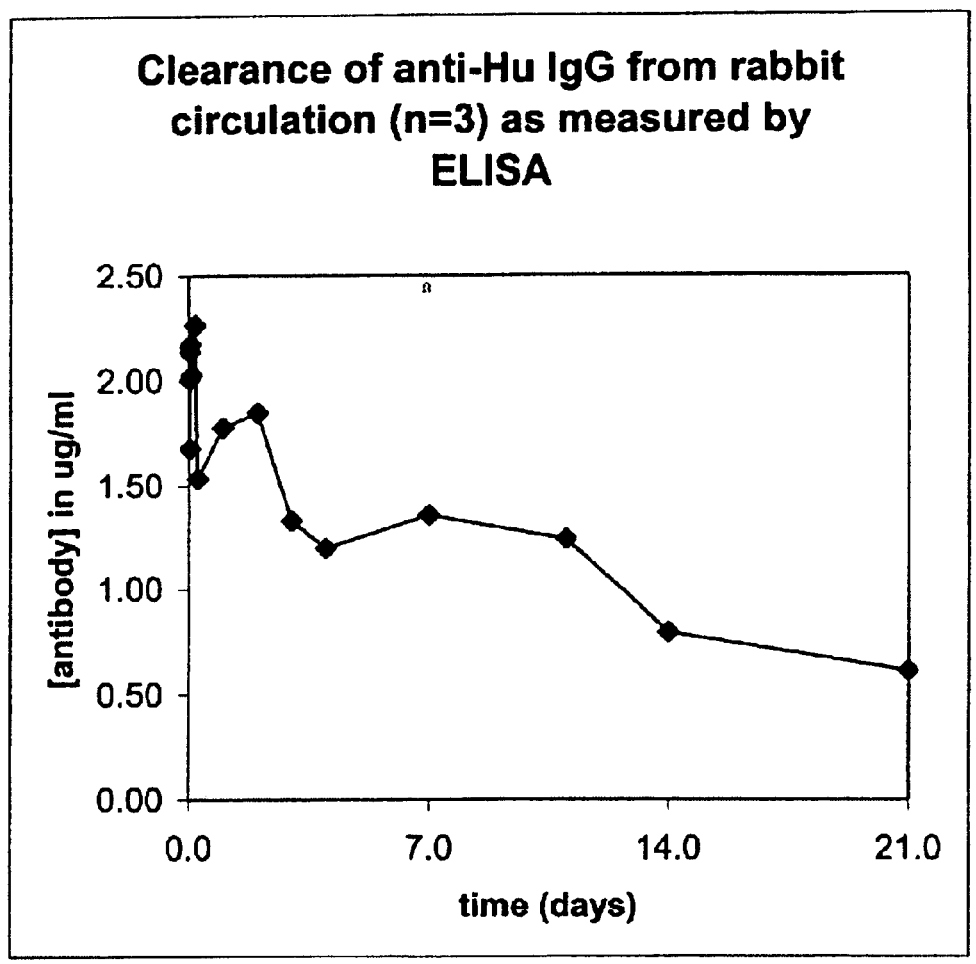
FIG. 18 shows clearance of rabbit-anti human IgG from rabbit circulation (n=3) as measured by ELISA. X-axis: time (days); Y-axis: antibody concentration in micrograms/ml.

When harvested samples are analyzed for rabbit anti-human IgG activity by ELISA the profile shown in FIG. 18 is obtained. The results demonstrate that the introduced antibody remains at detectable levels in circulation for up to 21 days and this would be well within the required time frame for ultrasound-mediated release studies. In addition the lowest detectable concentration of 0.6 µg/ml at day 21 suggests that loaded cells containing 100 µg of antibody are sufficient for the ultrasound-mediated release studies.

Example 18

Ultrasound-mediated release of payload from the erythrocyte delivery vehicle in vivo.

In order to demonstrate that ultrasound-mediated release of payload from the sensitized and loaded vehicle can be effected in vivo it was decided to sensitize and load rabbit erythrocytes with rabbit anti-human IgG. This is performed as described above for Example 15. Ultrasound sensitivity is confined prior to use and the cell population is shown to contain approximately 200 µg of antibody/ml of packed cells.

The recipient rabbit (3 kg) is anaesthetized by injecting 0.45 ml of Vetalar and 0.3 ml of Rompun sub-cutaneously into the back of the neck. Hair is removed from the abdominal area over the liver. Anesthesia is maintained by placing the animal on 2% isofluorane delivered via a face mask. A pre-injection sample of blood (50 µl) is taken and placed in 450 µl of PBS containing heparin. 0.5 ml of packed cells are then injected into the animal through the ear vein. The animal is rested for 10 minutes and another sample of blood is harvested. Ultrasound contact gel is liberally applied to the shaven area to mediate contact with a 1 MHz ultrasound head. Six 4-minute ultrasound treatments are applied on continuous wave delivery at 4 W/cm$^2$ with each treatment interrupted by 30 seconds within which a sample of blood is harvested. Following the six treatments the animal is rested for 20 minutes and two blood samples are taken at 10 minute intervals. Treatment is re-initiated at 60 minutes again at 4-minute intervals with 30-second rest intervals within which blood samples are taken. The animal is again rested after six treatments for a period of 30 minutes during which samples of blood are harvested at 10-minute intervals. The control animal consists of an animal into which a similar quantity of cells are injected and ultrasound treatment is withheld. Both animals are euthenized using pentobarbitone following treatment. Supernatants are harvested by centrifugation from all samples and subsequently assayed by ELISA to detect circulating rabbit anti-human IgG.

Results 18

Figure 19:
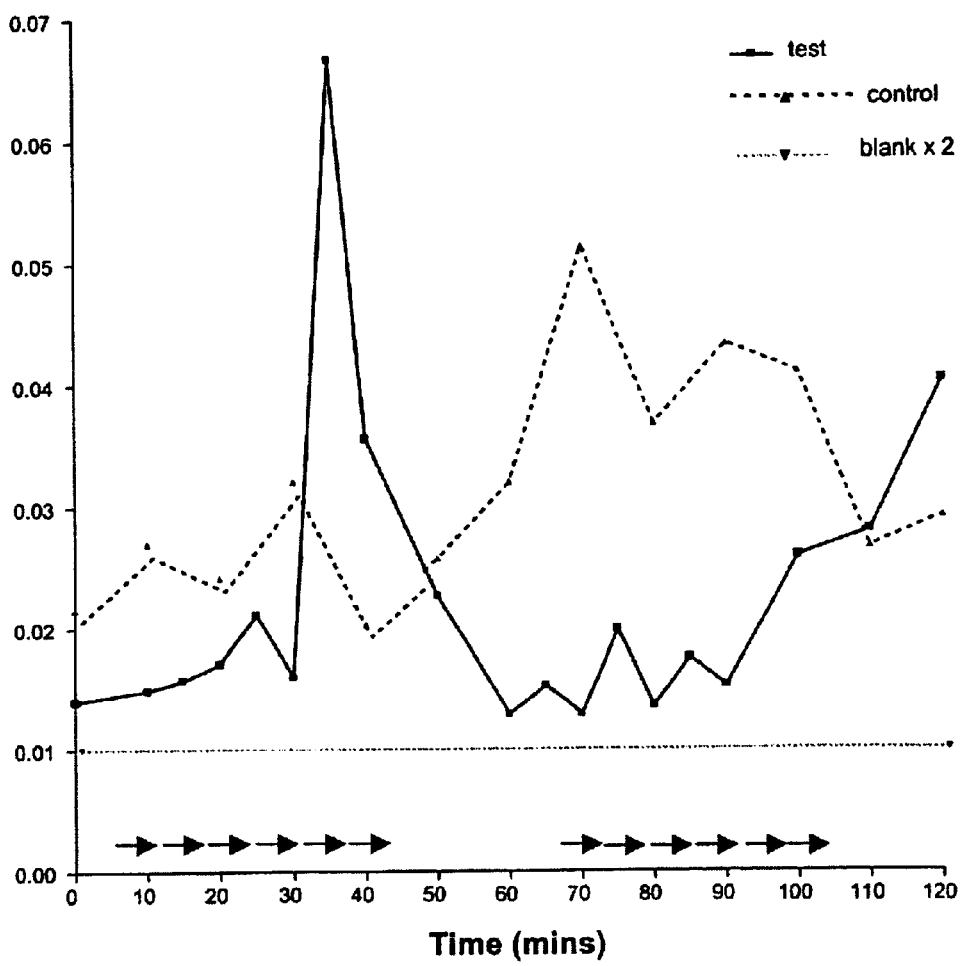
FIG. 19 shows ultrasound-mediated release of rabbit anti-human IgG from loaded and sensitized rabbit erythrocytes following exposure to ultrasound during circulation in vivo. X-axis: time (mins); Y-axis: antibody concentration in micrograms/ml. Filled squares (continuous —): test; filled upright triangles (black dashed -): control; filled inverted triangles (grey dashed -) represent pre-injection signal x 2; right-pointing arrows: ultrasound treatment periods (1 MHz probe, 4 W/cm$^2$, 4').

The results obtained during these experiments are shown in FIG. 19. Ultrasound treatments are indicated by the solid arrows and the dotted line traversing the lower portion of the curve represents the pre-injection background signal received from the ELISA. The results obtained from the ultrasound treated animal demonstrate the presence of antibody in circulation following 16 minutes treatment with ultrasound. After this period and during the rest period the amount of antibody in circulation decreases. However following the second phase of treatments initiated at 60 minutes the antibody concentration again begins to rise. In the control animal the level of antibody in circulation does not exhibit this pattern. It is interesting to note that the level of antibody in the first peak appearing in the ultrasound-treated animal accounts for approximately 16–20% of the total antibody contained in vehicle injected into the animal. This suggests that the remainder of antibody-containing vehicle supplies a sufficient reservoir for release as indicated by the second peak at 120 minutes. These results demonstrate ultrasound-mediated release of a payload from the sensitized and loaded vehicle in vivo.

All publications mentioned in the above specification are herein incorporated by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A method for selectively releasing an agent from a red blood cell comprising the steps of:
    (a) loading the red blood cell with the agent in vitro or ex-vivo;
    (b) sensitising in vitro or ex-vivo the red blood cell by exposing it to an electric field; and
    (c) causing the agent to be released from the loaded and sensitised red blood cell by applying ultrasound at a frequency and energy sufficient to cause disruption of the loaded and sensitized red blood cell but insufficient to cause disruption of unsensitised red blood cells.

2. The method according to claim 1, wherein the sensitising comprises the step of applying an electric pulse to the red blood cell.

3. The method according to claim 1, in which the sensitisation of the red blood cell precedes the loading of the agent.

4. The method according to claim 1, in which the loading of the agent precedes the sensitisation of the red blood cell.

5. The method according to claim 1, in which the sensitisation of the red blood cell and the loading of the agent are simultaneous.

6. The method according to claim 1, in which the electric field is applied as an electric pulse from about 0.1 kVolts/cm to about 10 kVolts/cm under in vitro conditions.

7. The method according to claim 6, in which the electric pulse is applied for between 1 $\mu$s and 100 milliseconds.

8. The method according to claim 1, in which the ultrasound is selected from the group consisting of diagnostic ultrasound, therapeutic ultrasound and a combination of diagnostic and therapeutic ultrasound.

SEQUENCE LISTING

```
<160> NUMBER OF SEQ ID NOS: 3

<210> SEQ ID NO 1
<211> LENGTH: 9
<212> TYPE: PRT
<213> ORGANISM: Human immunodeficiency virus

<400> SEQUENCE: 1

Arg Lys Lys Arg Arg Gln Arg Arg Arg
1               5

<210> SEQ ID NO 2
<211> LENGTH: 15
<212> TYPE: PRT
<213> ORGANISM: Human immunodeficiency virus

<400> SEQUENCE: 2

Cys Gly Arg Lys Lys Arg Arg Gln Arg Arg Arg Pro Pro Gln Cys
1               5                   10                  15

<210> SEQ ID NO 3
<211> LENGTH: 16
<212> TYPE: PRT
<213> ORGANISM: Drosophila sp.

<400> SEQUENCE: 3

Arg Gln Ile Lys Ile Trp Phe Gln Asn Arg Arg Met Lys Trp Lys Lys
1               5                   10                  15
```

9. The method according to claim 8, in which the ultrasound is applied by an ultrasound energy source at a power level of from about 0.05 W/cm² to about 100 W/cm².

10. A method for delivering an agent to a target site in a vertebrate, comprising the steps of:
(a) loading a red blood cell with the agent in vitro or ex-vivo;
(b) sensitising in vitro or ex-vivo the red blood cell by exposing it to an electric field;
(c) introducing the loaded and sensitized red blood cell to the target site in a vertebrate by transfusion or infusion; and
(d) causing the agent to be released from the loaded and sensitised red blood cell by applying ultrasound at a frequency and energy sufficient to cause disruption of the loaded and sensitised red blood cell but insufficient to cause disruption of unsensitised red blood cells.

11. The method according to claim 10, in which the red blood cell of step (c) comprises polyethylene glycol on its surface.

12. The method according to claim 10, in which the vertebrate is a mammal.

13. The method according to claim 1 or 10, in which the loading of the agent is simultaneous with the sensitisation of the red blood cell.

14. The method according to claim 1 or 10, in which the sensitisation of the red blood cell precedes the loading of the agent.

15. The method according to claim 1 or 10, in which the loading of the agent precedes the sensitisation of the red blood cell.

16. The method according to claim 1 or 10, in which the loading is performed by a procedure selected from a group consisting of electroporation, sonoporation, microinjection, membrane intercalation, microparticle bombardment, lipid-mediated transfection, osmosis, osmotic pulsing, diffusion, endocytosis, and crosslinking to a red blood cell surface component.

17. The method according to claim 1 or 10, in which the agent is a polypeptide, a nucleic acid, or a virus.

18. The method according to claim 17, in which the agent is combined with an imaging agent.

* * * * *